(12) United States Patent
Fujihara et al.

(10) Patent No.: US 7,723,495 B2
(45) Date of Patent: May 25, 2010

(54) AMIDITE FOR NUCLEIC ACID SYNTHESIS AND NUCLEIC ACID SYNTHESIZING METHOD

(75) Inventors: Tsuyoshi Fujihara, Kawasaki (JP); Shozo Fujita, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 244 days.

(21) Appl. No.: 11/987,168

(22) Filed: Nov. 28, 2007

(65) Prior Publication Data
US 2008/0167459 A1    Jul. 10, 2008

(30) Foreign Application Priority Data
Jan. 5, 2007    (JP) .............................. 2007-000576

(51) Int. Cl.
*C07H 19/00*    (2006.01)
*C07H 21/00*    (2006.01)
(52) U.S. Cl. .................... 536/22.1; 536/18.7; 536/25.3; 536/25.31; 536/25.32; 536/26.1
(58) Field of Classification Search ........................ None
See application file for complete search history.

(56) References Cited

OTHER PUBLICATIONS

Heikkilä, et al.: "The 9-Fluorenylmethoxycarbonyl (Fmoc) Group for the Protection of Amino Functions of Cytidine, Adenosine, Guanosine and Their 2'-Deoxysugar Derivatives." Acta Chem. Scand., B37, 1983, pp. 263-265; see p. 2 of specification.

Koole, et al.: "Synthesis of Phosphate-Methylated DNA Fragments Using 9-Fluorenylmethoxycarbonyl as Transient Base Protecting Group." J. Org. Chem. 1989, 54, pp. 1657-1664; see p. 2 of specification.

Kuijpers, et al.: "The 2-(Acetoxymethyl)Benzoyl (AMB) Group as a New Base-Protecting Group, Designed for the Protection of (Phosphate) Modified Oligonucleotides." Tetrahedron Letters, vol. 31, No. 46, 1990, pp. 6729-6732; see p. 2 of specification.

Eritja, et al.: "A Synthetic Procedure for the Preparation of Oligonucleotides without Using Ammonia and Its Application for the Synthesis of Oligonucleotides Containing O-4-Alkyl Thymidines." Tetrahedron vol. 48, No. 20, 1992, pp. 4171-4182; see p. 2 of specification.

Aviñó, et al.: "Use of NPE-Protecting Groups for the Preparation of Oligonucleotides without Using Nucleophiles During the Final Deprotection." Nucleosides & Nucleotides, 13(10), 1994, pp. 2059-2069; see p. 2 of specification.

Kuijpers, et al.: "The Application of the AMB Protective Group in the Solid-Phase Synthesis of Methylphosphonate DNA Analogues." Nucleic Acids Research, vol. 21, No. 15, 1993, pp. 3493-3500; see p. 2 of specification.

*Primary Examiner*—Patrick T Lewis
(74) *Attorney, Agent, or Firm*—Kratz, Quintos & Hanson, LLP

(57) ABSTRACT

To provide an amidite for nucleic acid synthesis, which enables a protective group therein to be removed under moderate conditions and can be practically used, and a nucleic acid synthesizing method using the amidite for nucleic acid synthesis. Specifically, the present invention relates to an amidite for nucleic acid synthesis represented by General Formula (I) below, and a nucleic acid synthesizing method using the amidite for nucleic acid synthesis:

General Formula (I)

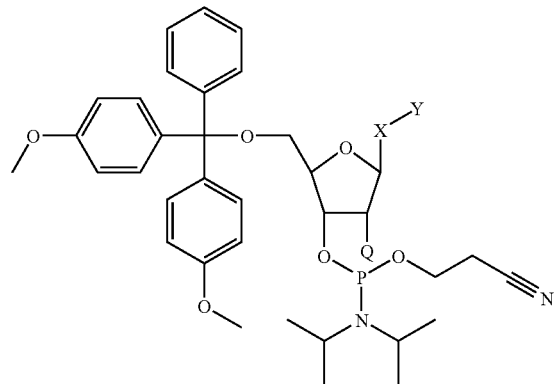

where X denotes a base; Y denotes a protective group formed of any one of a 4-aminobutyric acid derivative, an o-aminomethylbenzoic acid derivative, an o-aminophenylacetic acid derivative, an o-aminoethylbenzoic acid derivative, an o-aminomethylphenylacetic acid derivative, an o-aminophenylpropionic acid derivative and a 5-aminovaleric acid derivative; and Q denotes one of a hydrogen atom and a hydroxyl group.

19 Claims, 16 Drawing Sheets

Structural Formula (4)

Structural Formula (5)

Structural Formula (6)

Structural Formula (7)

Structural Formula (8)

Structural Formula (9)

Structural Formula (10)

Structural Formula (11)

Structural Formula (12)

AMIDITE FOR NUCLEIC ACID SYNTHESIS AND NUCLEIC ACID SYNTHESIZING METHOD

CROSS-REFERENCE TO RELATED APPLICATIONS

This application is based upon and claims the benefits of the priority from the prior Japanese Patent Application No. 2007-000576 filed on Jan. 5, 2007, the entire contents of which are incorporated herein by reference.

BACKGROUND OF THE INVENTION

1. Field of the Invention

The present invention relates to an amidite for nucleic acid synthesis suitable for synthesizing a nucleic acid, and a nucleic acid synthesizing method using the amidite.

2. Description of the Related Art

Solid-phase synthesis of nucleic acids was initiated as long ago as more than 20 years, and automatic synthesizers were already sold then. Solid-phase synthesis of a nucleic acid is carried out, for example by making a nucleic acid material (amidite) combine in a condensation reaction with a solid carrier (e.g. CPG) in which a nucleoside is immobilized; this condensation reaction needs to take place, with only a phosphoric acid portion in the amidite and a hydroxyl group in another amidite being involved in the condensation reaction, and other reactive groups not being involved in the condensation reaction. Therefore, it is necessary to prevent an exocyclic amino group, etc. contained in a base of an amidite used from being involved in the condensation reaction by introducing a protective group, and to eliminate (remove) the protective group after the condensation reaction has finished completely. Conventionally, benzoyl group, isobutyryl group and the like have been used for protective groups introduced into exocyclic amino groups in bases, and a method of allowing concentrated ammonia water to act at 55° C. for 8 hr to 15 hr so as to remove these protective groups has been common.

However, for example, in order to modify functional artificial nucleic acids such as primers, probes, antisense DNAs, siRNAs, etc. with fluorescent labels or the like, improved amidites which make it possible to remove a protective group and obtain a nucleic acid under more moderate conditions are hoped for. For example, in the related art, amidites for nucleic acid synthesis represented by Structural Formulae (4) to (6) in FIG. 14 have been reported as nucleic acid amidites which enable protective groups therein to be removed by diazabicycloundecene (DBU) that is a bulky base (refer to Acta Chem, Scand., B37, 263 (1983) and J. Org. Chem., 54, 1657 (1989)). However, since the amidites for nucleic acid synthesis represented by Structural Formulae (4) to (6) are unstable in acetonitrile that is an aprotic solvent (refer to Tetrahedron Letters 46, 6729 (1990)), they are not suitable for practical use. Additionally, although it has also been reported that amidites for nucleic acid synthesis represented by Structural Formulae (7) to (9) in FIG. 15 enable protective groups therein to be removed under moderate conditions (in pyridine, 0.5M, DBU, 16 hr) (refer to Tetrahedron 40, 4171 (1992) and Nucleodied & Nuclrotides 13, 2059 (1994)), they are problematic in that nucleic acid bases are alkylated owing to highly-concentrated DBU and deprotection for a long period of time. In addition, although it has also been reported that amidites for nucleic acid synthesis represented by Structural Formulae (10) to (12) in FIG. 16 enable protective groups therein to be removed under moderate conditions (in methanol, $K_2CO_3$) (refer to Tetrahedron Letters 46, 6729 (1990) and Nucleic Acids Research 21, 3493 (1993)), they are problematic in that esters, etc. decompose because $K_2CO_3$ that is a base is used in methanol that is a protic solvent.

Thus, as things stand at present, development of an amidite for nucleic acid synthesis which enables a protective group therein to be removed under moderate conditions and can be practically used, and of a nucleic acid synthesizing method using the amidite for nucleic acid synthesis is still hoped for.

BRIEF SUMMARY OF THE INVENTION

According to one aspect, the amidite for nucleic acid synthesis is characterized in that it is represented by General Formula (I) below. Note that in General Formula (I) below, X denotes a base; Y denotes a protective group formed of any one of a 4-aminobutyric acid derivative, an o-aminomethylbenzoic acid derivative, an o-aminophenylacetic acid derivative, an o-aminoethylbenzoic acid derivative, an o-aminomethylphenylacetic acid derivative, an o-aminophenylpropionic acid derivative and a 5-aminovaleric acid derivative; and Q denotes one of a hydrogen atom and a hydroxyl group.

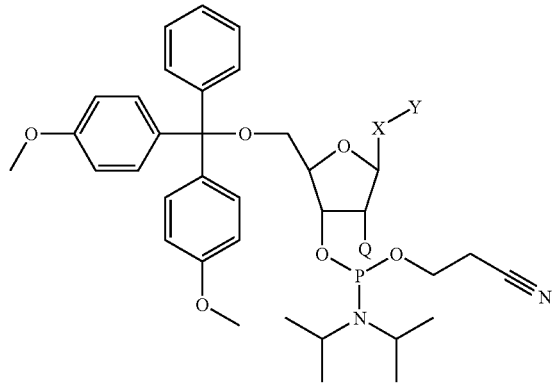

General Formula (I)

According to another aspect, the nucleic acid synthesizing method is characterized by using the amidite for nucleic acid synthesis.

DETAILED DESCRIPTION OF THE INVENTION

Amidite for Nucleic Acid Synthesis

Figure 1:
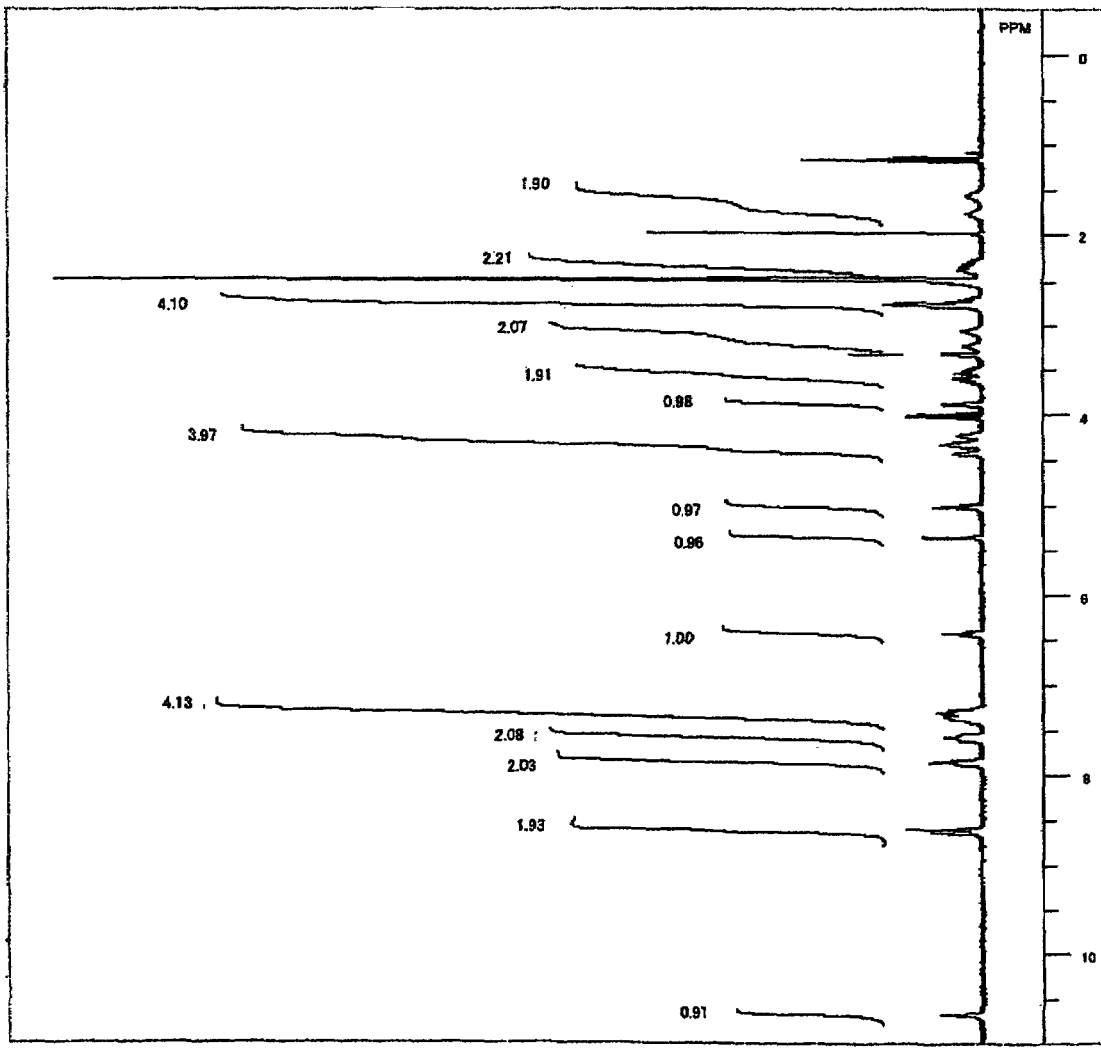
FIG. 1 shows a $^1$H-NMR spectrum of a compound Ia in Example 1.
Figure 2:
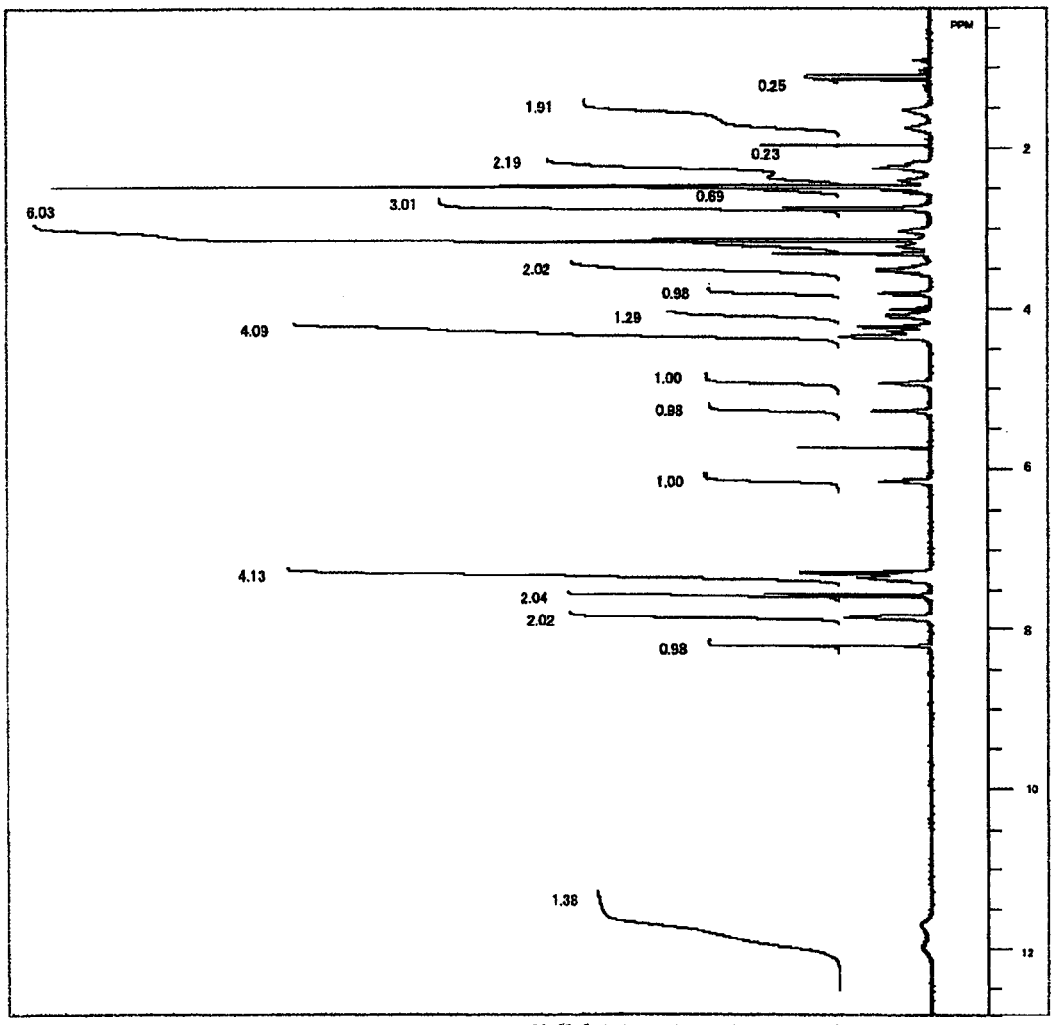
FIG. 2 shows a $^1$H-NMR spectrum of a compound Ig in Example 1.
Figure 3:
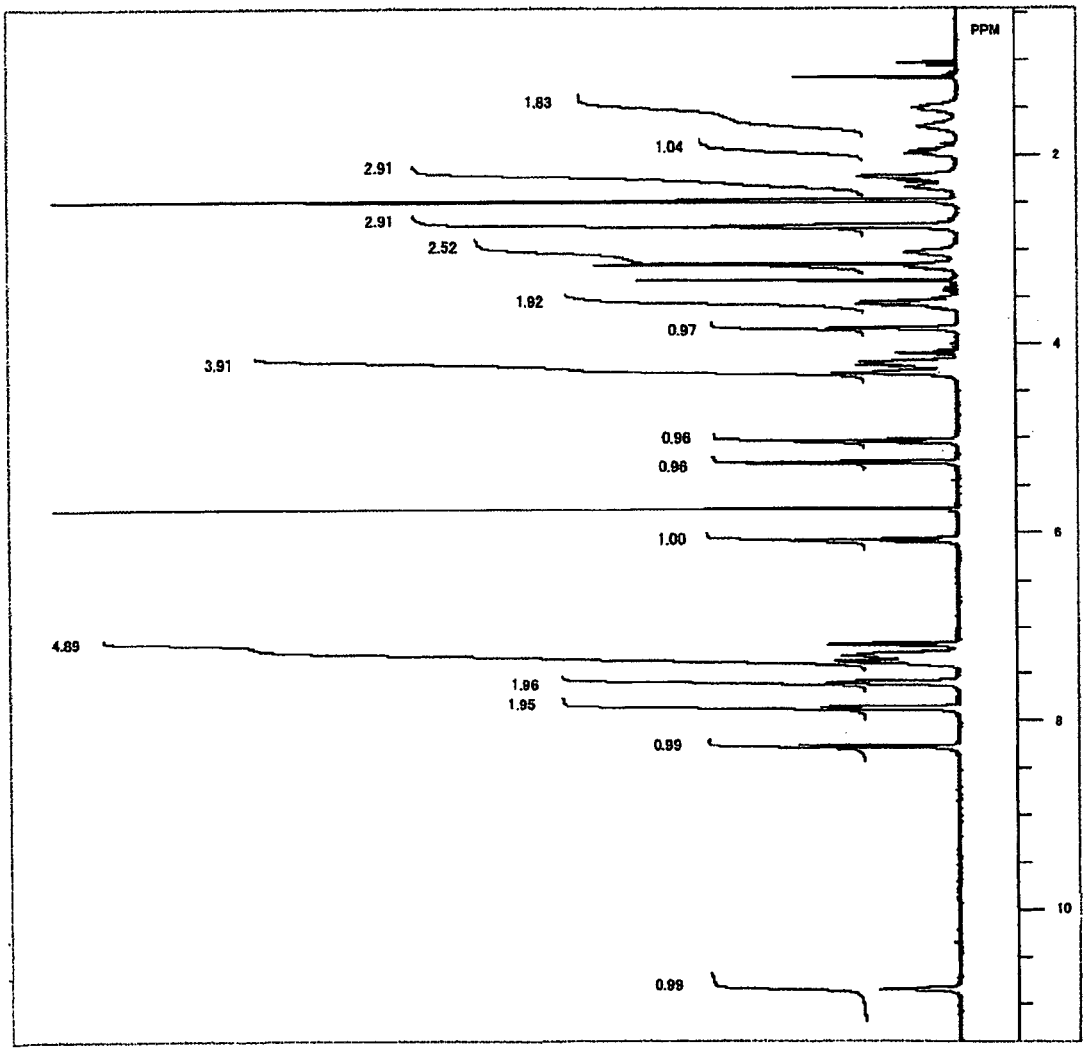
FIG. 3 shows a $^1$H-NMR spectrum of a compound Ic in Example 1.
Figure 4:
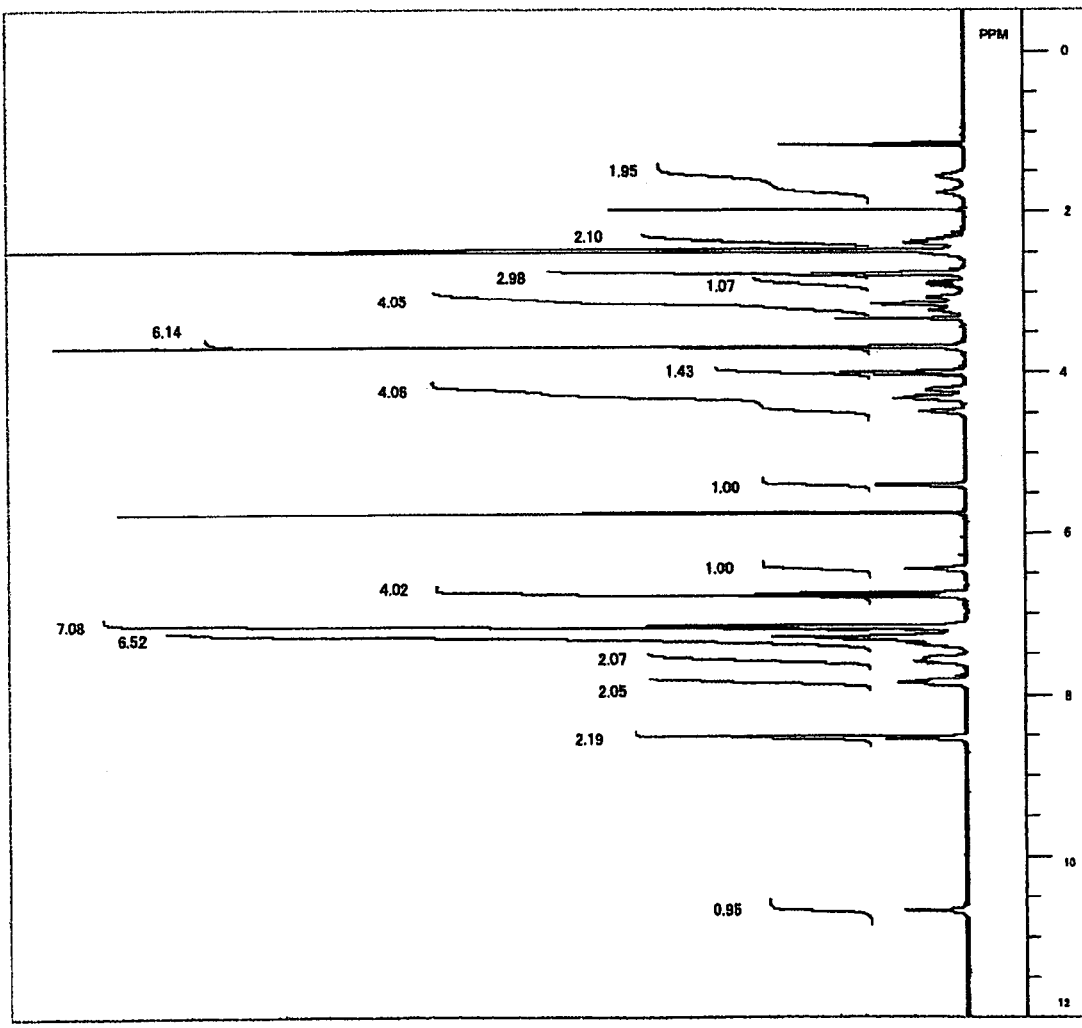
FIG. 4 shows a $^1$H-NMR spectrum of a compound IIa in Example 1.
Figure 5:
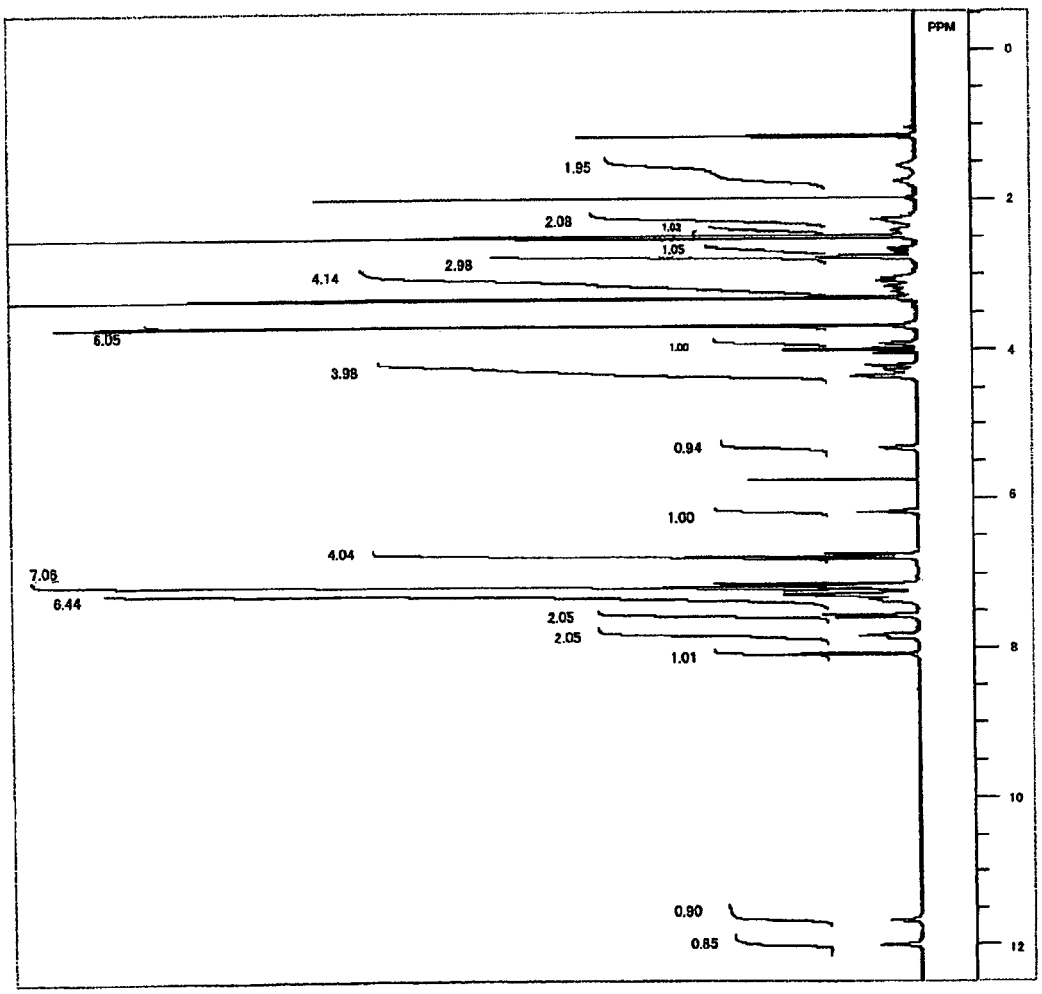
FIG. 5 shows a $^1$H-NMR spectrum of a compound IIg in Example 1.
Figure 6:
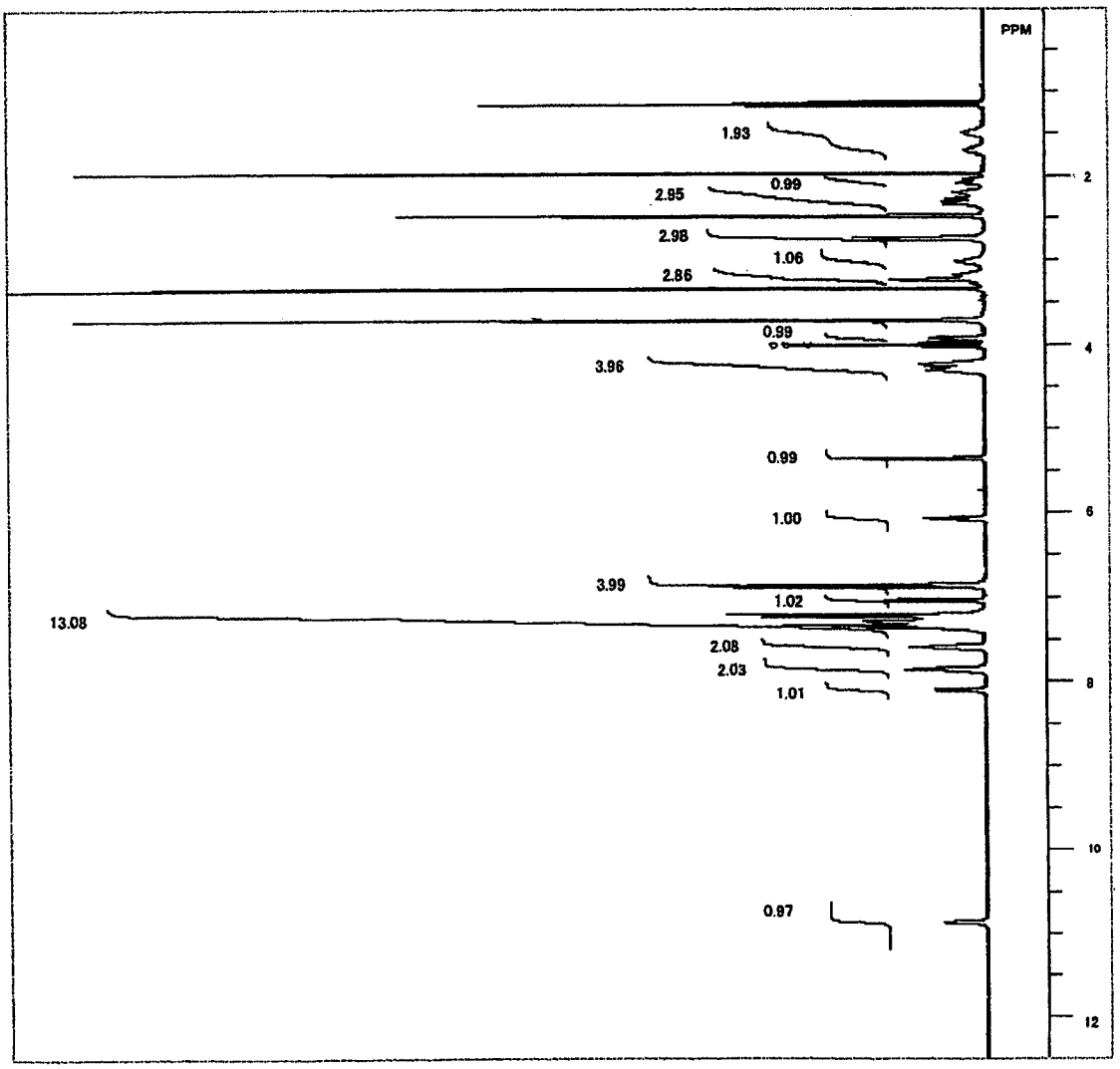
FIG. 6 shows a $^1$H-NMR spectrum of a compound IIc in Example 1.
Figure 7:
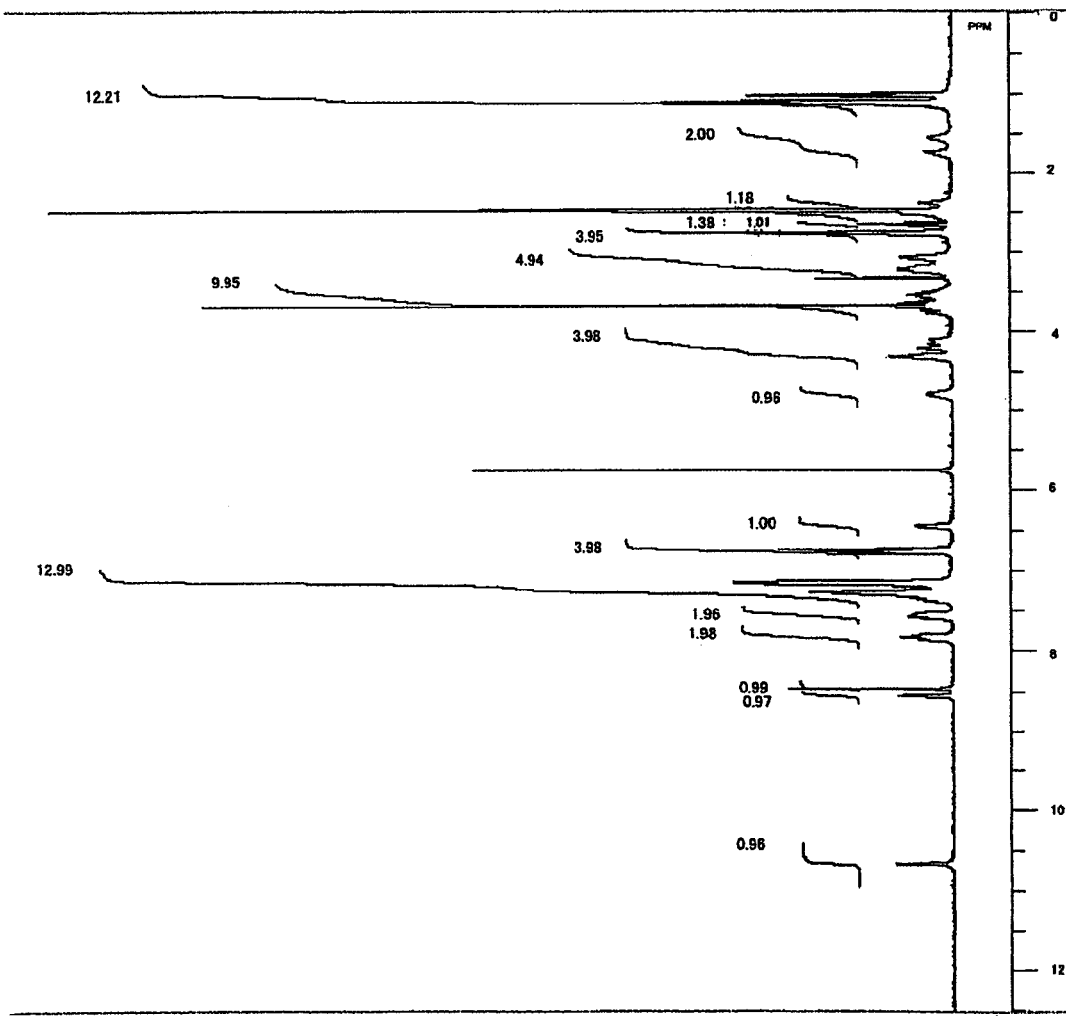
FIG. 7 shows a $^1$H-NMR spectrum of a compound IIIa (amidite for nucleic acid synthesis represented by Structural Formula (I)) in Example 1.
Figure 8:
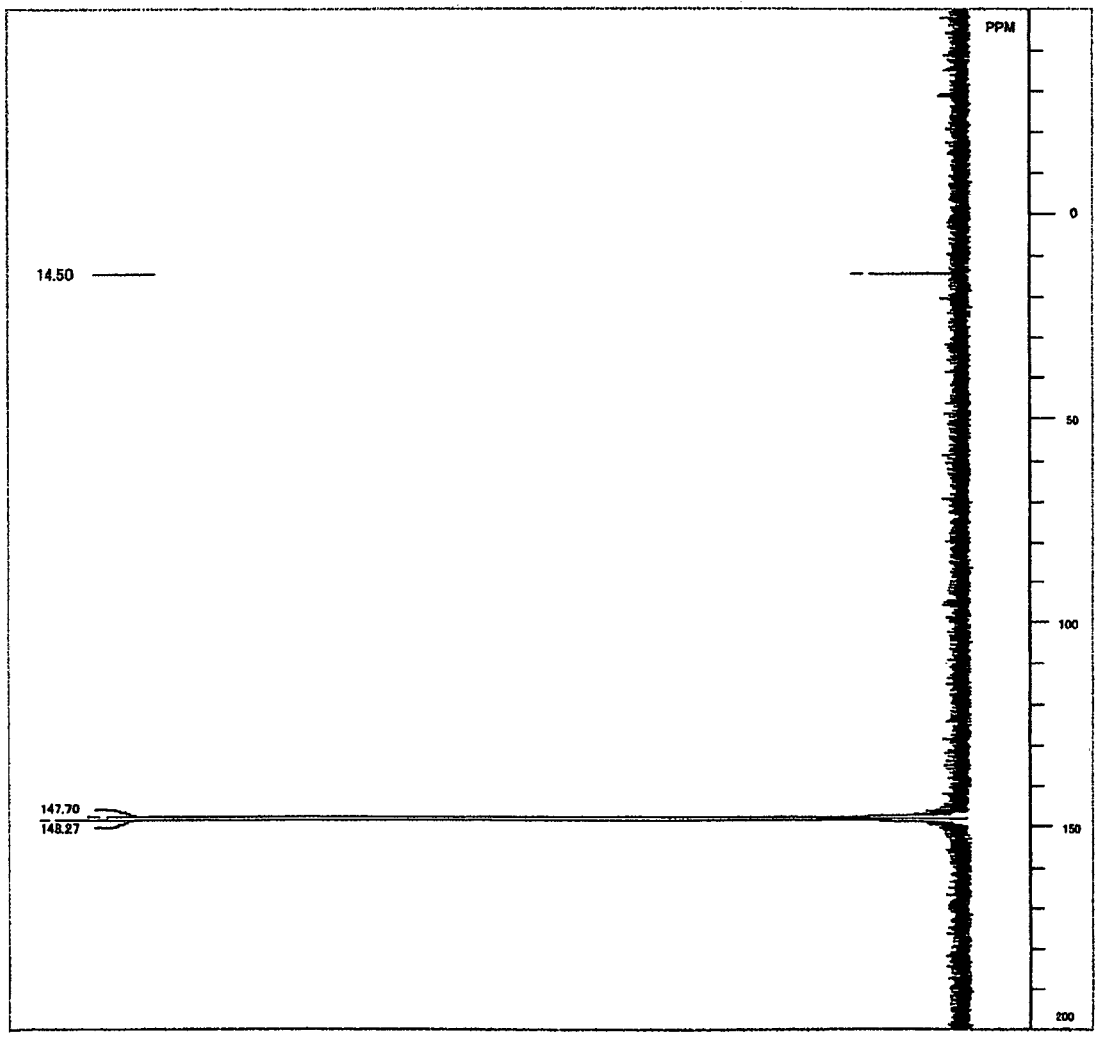
FIG. 8 shows a $^{31}$P-NMR spectrum of a compound IIIa (amidite for nucleic acid synthesis represented by Structural Formula (I)) in Example 1.
Figure 9:
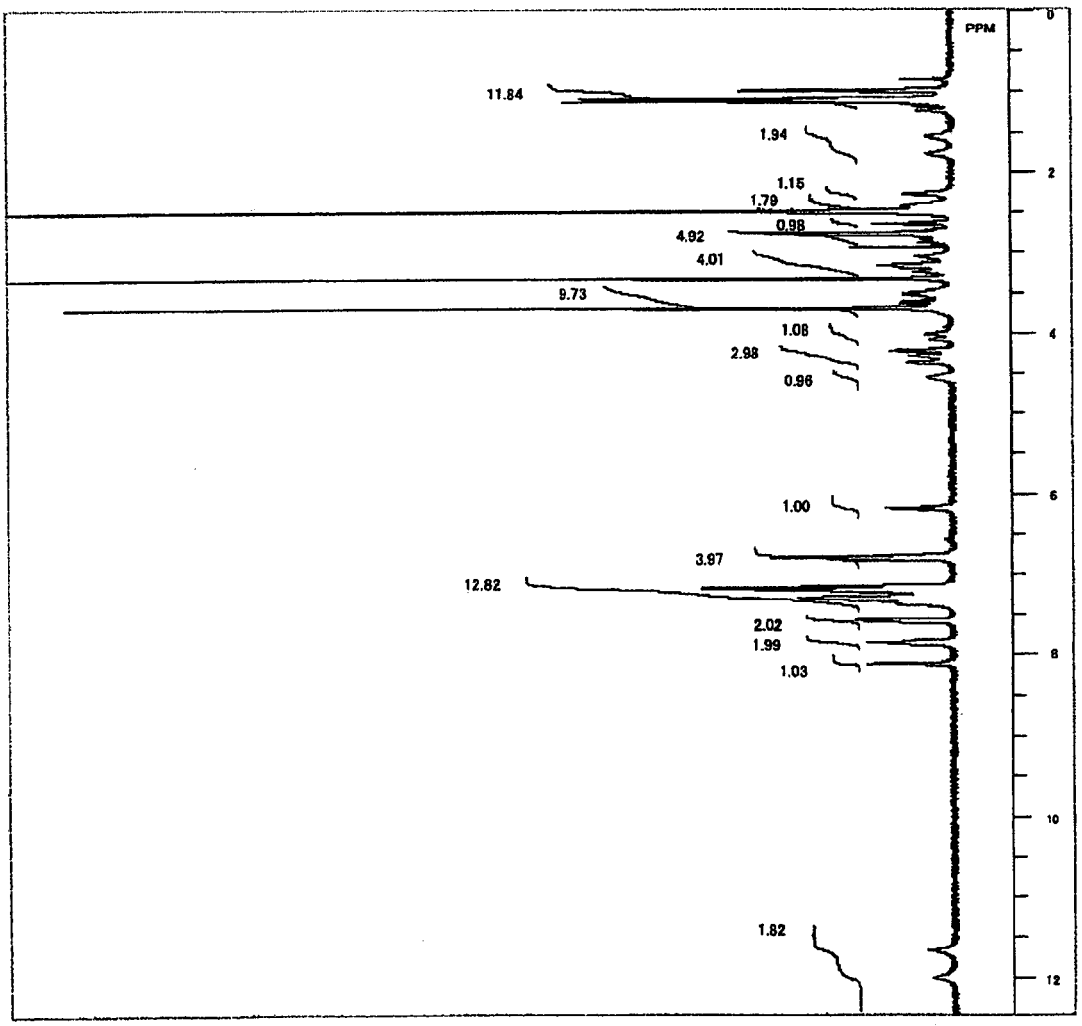
FIG. 9 shows a $^1$H-NMR spectrum of a compound IIIg (amidite for nucleic acid synthesis represented by Structural Formula (2)) in Example 1.
Figure 10:
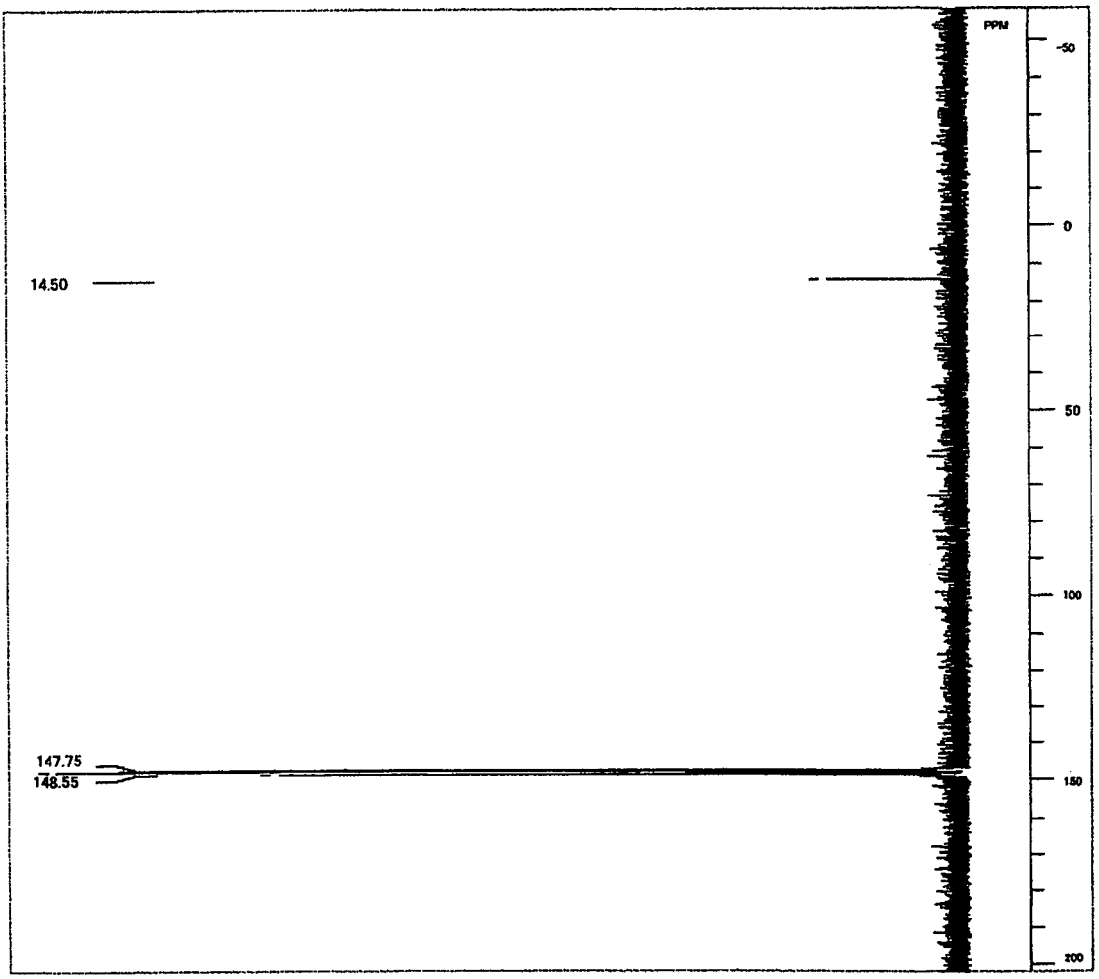
FIG. 10 shows a $^{31}$P-NMR spectrum of a compound IIIg (amidite for nucleic acid synthesis represented by Structural Formula (2)) in Example 1.
Figure 11:
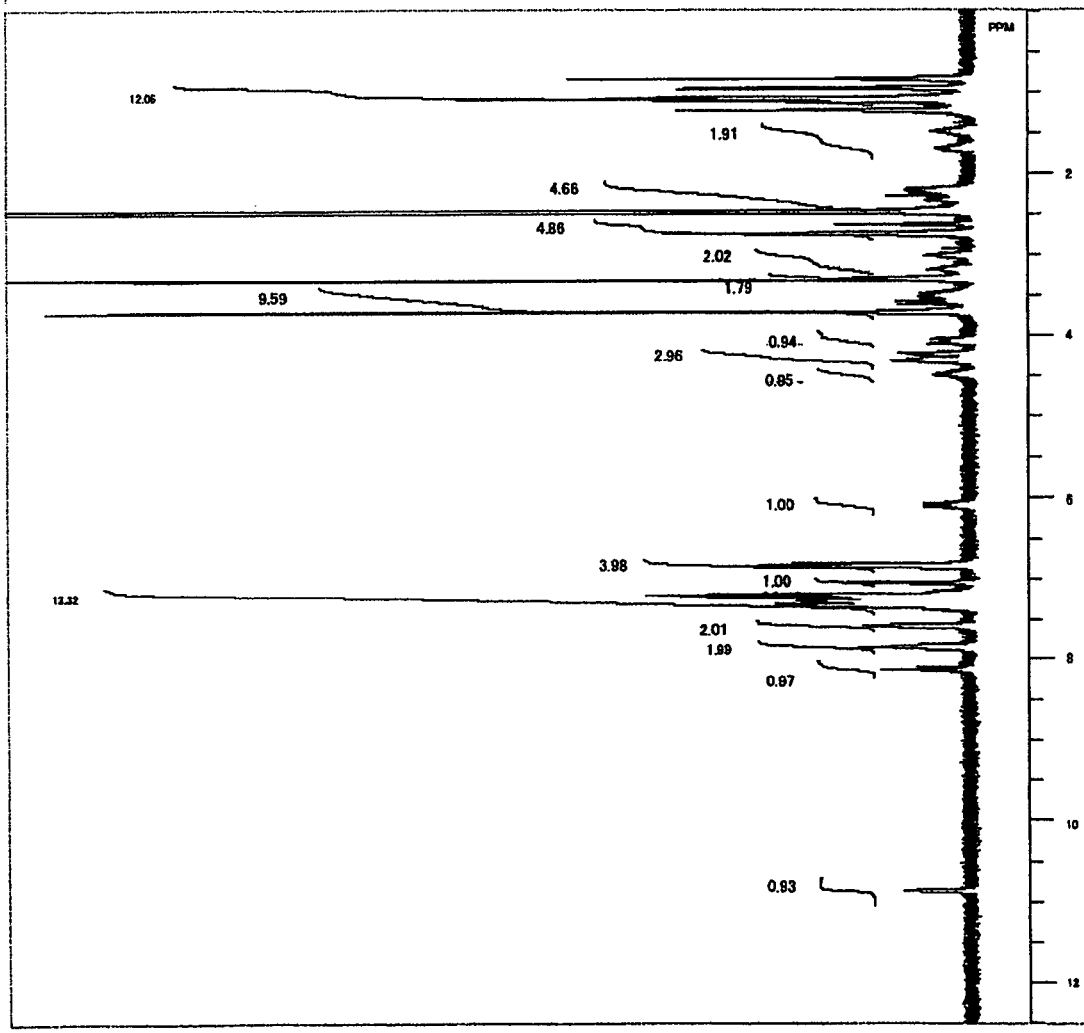
FIG. 11 shows a ¹H-NMR spectrum of a compound IIIc (amidite for nucleic acid synthesis represented by Structural Formula (3)) in Example 1.
Figure 12:
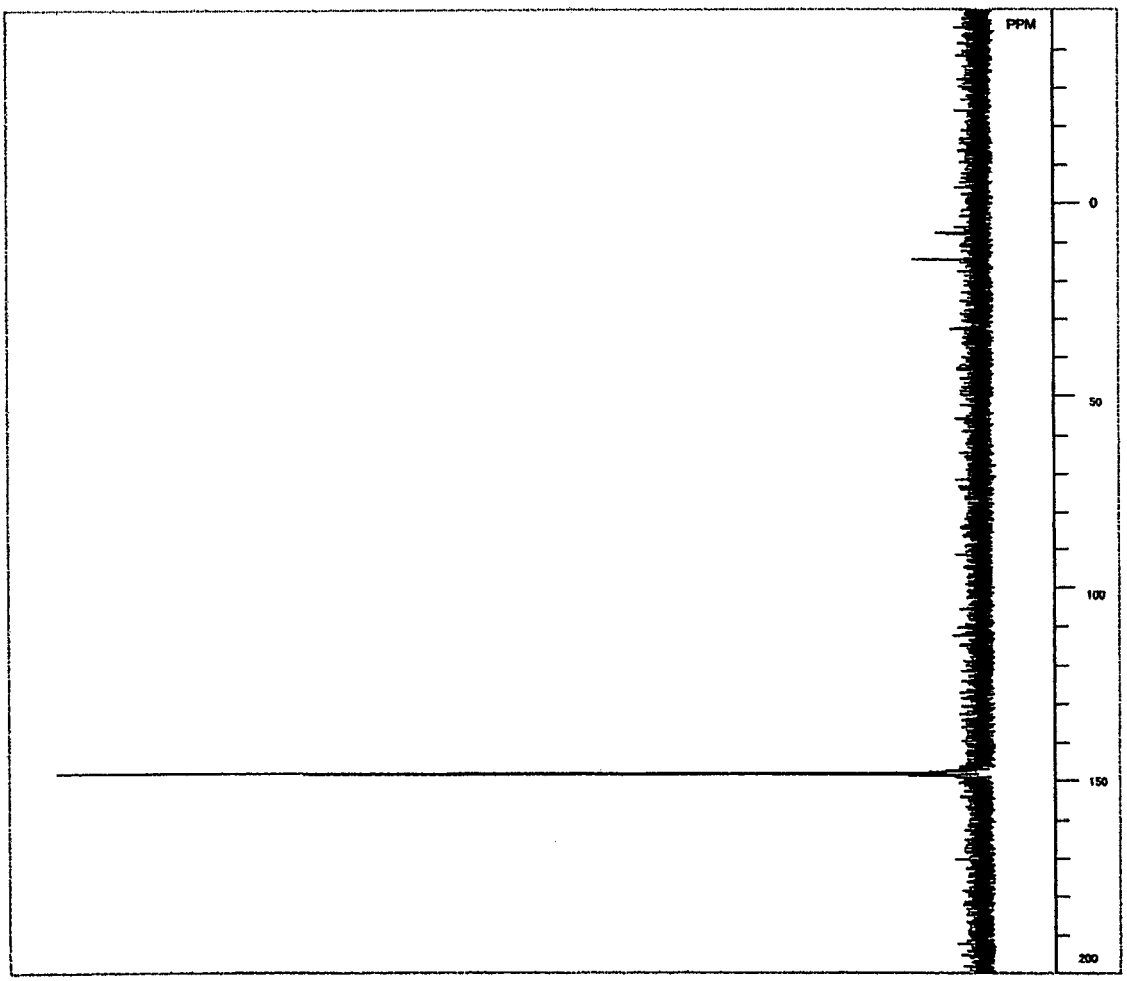
FIG. 12 shows a ³¹P-NMR spectrum of a compound IIIc (amidite for nucleic acid synthesis represented by Structural Formula (3)) in Example 1.

The amidite for nucleic acid synthesis of the present invention is characterized in that it is represented by General Formula (I) below.

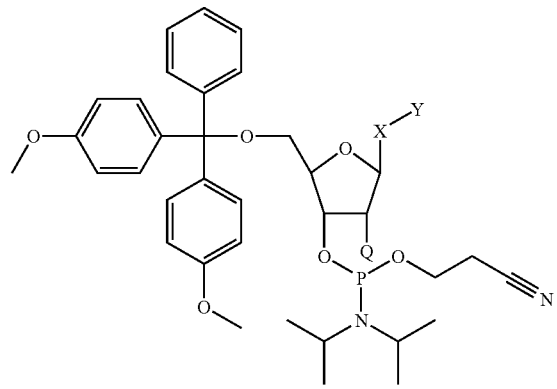

General Formula (I)

where X denotes a base; Y denotes a protective group formed of any one of a 4-aminobutyric acid derivative, an o-aminomethylbenzoic acid derivative, an o-aminophenylacetic acid derivative, an o-aminoethylbenzoic acid derivative, an o-aminomethylphenylacetic acid derivative, an o-aminophenylpropionic acid derivative and a 5-aminovaleric acid derivative; and Q denotes one of a hydrogen atom and a hydroxyl group.

In General Formula (I) above, the base denoted by X is not limited to particular bases, and a suitable one can be selected according to the purpose; examples thereof include adenine (A), guanine (G) and cytosine (C).

In General Formula (I) above, the protective group denoted by Y is formed of any one of a 4-aminobutyric acid derivative, an o-aminomethylbenzoic acid derivative, an o-aminophenylacetic acid derivative, an o-aminoethylbenzoic acid derivative, an o-aminomethylphenylacetic acid derivative, an o-aminophenylpropionic acid derivative and a 5-aminovaleric acid derivative; the protective group denoted by Y is not limited to particular protective groups, and a suitable one can be selected according to the purpose, but a protective group represented by General Formula (II) below is more favorable as a specific example thereof.

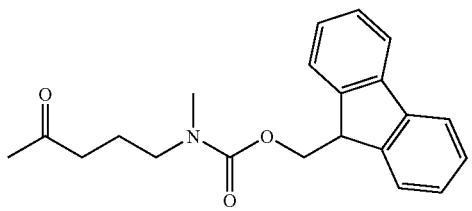

General Formula (II)

It is desirable that the protective group be bonded to an exocyclic amino group in the base, for example to the C-6 position of an adenine base, the C-2 position of a guanine base or the C-6 position of a cytosine base.

The amidite for nucleic acid synthesis is not limited to particular amidites, and a suitable one can be selected for the amidite according to the purpose; specific examples thereof include amidites for nucleic acid synthesis represented by Structural Formulae (1) to (3) below.

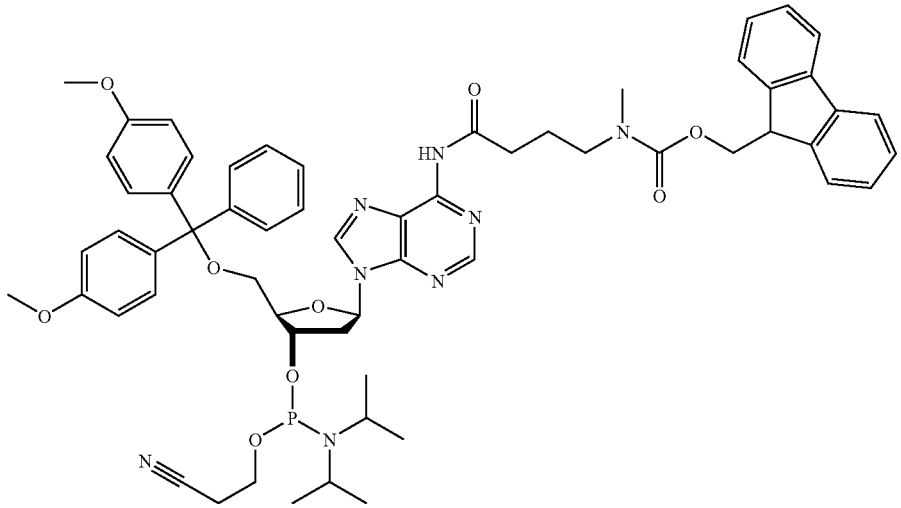

Structural Formula (1)

-continued

Structural Formula (2)

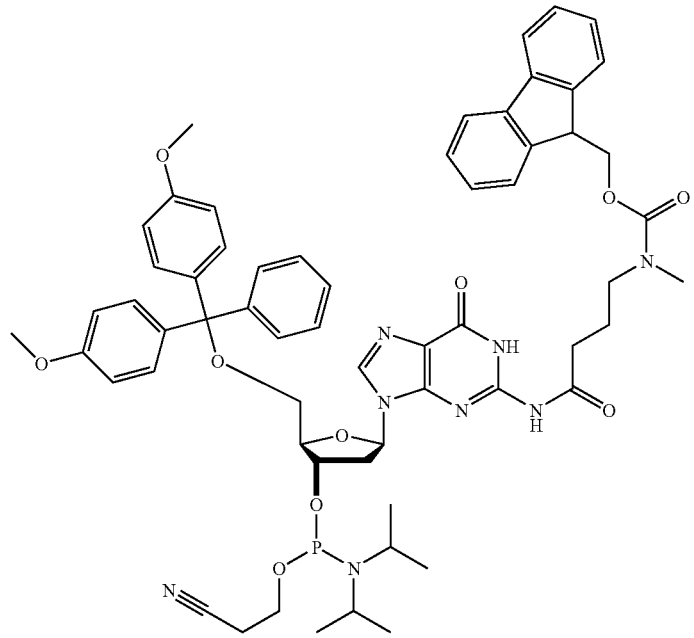

Structural Formula (3)

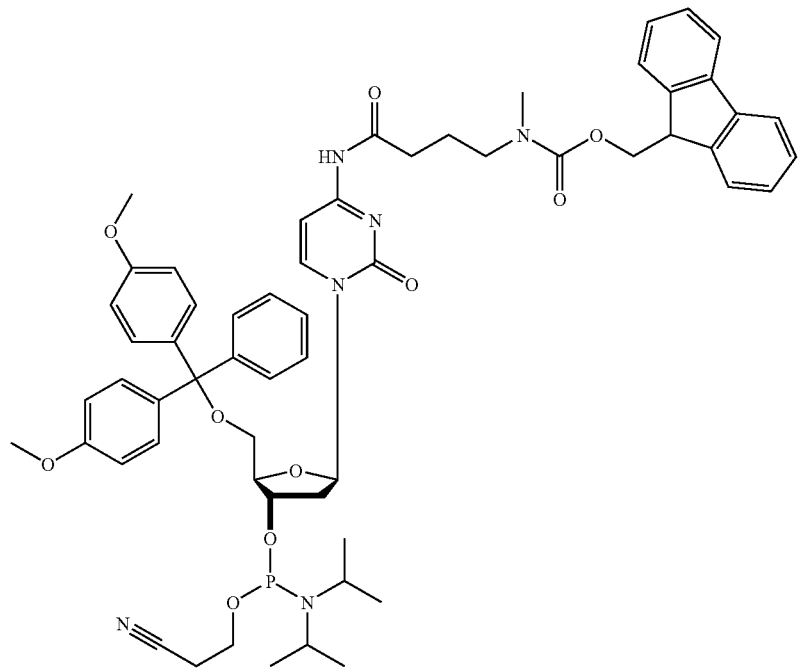

The synthesizing method of the amidite for nucleic acid synthesis is not limited to particular synthesizing methods; examples thereof include a synthesizing method later described in Examples.

In the amidite for nucleic acid synthesis, the protective group can be removed under moderate conditions.

The fact that "the protective group can be removed under moderate conditions" is not particularly restricted, and suitable moderate conditions can be selected according to the purpose; for example, the protective group can be removed by a bulky base in an aprotic solvent. The aprotic solvent is not limited to particular aprotic solvents, and a suitable one can be selected according to the purpose; examples thereof include acetonitrile, dichloromethane, DMF (N,N-dimethylformamide) and N-methylpyrrolidone. The bulky base is not limited to particular bulky bases, and a suitable one can be selected according to the purpose; examples thereof include DBU (1,8-diazabicyclo[5.4.0]-7-undecene), DBN (1,5-diazabicyclo[4.3.0]-5-nonene) and tetramethylguanidine. It is desirable that the protective group be removed by DBU in acetonitrile amongst these bulky bases and these aprotic solvents. Additionally, in this case, it is desirable that the concentration of DBU required to remove the protective group be 0.5M or less, more desirably 0.1M or less, even more desirably 0.01M or less; it is desirable that the time required be 8 hr or less, more desirably 1 hr or less, even more desirably 15 min or less.

Since all of the amidites for nucleic acid synthesis make it possible to remove the protective group under such moderate conditions as described above, they can be suitably used for the after-mentioned nucleic acid synthesizing method of the present invention, for example. It should be noted that each of the amidites for nucleic acid synthesis may be used alone, or two or more of them may be used together. The amidites for nucleic acid synthesis are advantageous in that all of them make it possible to remove the protective group under such moderate conditions as described above, regardless of types of bases (adenine, guanine and cytosine).

(Nucleic Acid Synthesizing Method)

The nucleic acid synthesizing method of the present invention is characterized by using the amidite for nucleic acid synthesis of the present invention.

The nucleic acid synthesizing method is not limited to a particular synthesizing method, and a suitable one can be selected according to the purpose as long as it uses the amidite for nucleic acid synthesis; examples thereof include a conventional nucleic acid synthesizing method in which a solid-phase method is combined with a diester method, a triester method, a phosphite method, a phosphoramidite method, an H-phosphonate method, a thiophosphite method or the like. Also, the nucleic acid synthesis can be conducted using a conventional automatic nucleic acid synthesizer, for example.

As to amidites for nucleic acid synthesis used in the nucleic acid synthesizing method, A amidite, G amidite and C amidite used may consist entirely of the amidites for nucleic acid synthesis of the present invention, or the A amidite, G amidite and C amidite used may consist partly of the amidites for nucleic acid synthesis of the present invention; however, it is particularly desirable that the A amidite, G amidite and C amidite consist entirely of the amidites for nucleic acid synthesis of the present invention.

For example, when a nucleic acid obtained by the nucleic acid synthesizing method is used as a PCR primer or the like, protective groups in all amidites for nucleic acid synthesis need to be removed similarly to one another at a stage where the primer is actually applied to PCR, etc.; however, in the nucleic acid synthesizing method, if A amidite, G amidite and C amidite other than the amidites for nucleic acid synthesis of the present invention are used as a part of amidites, deprotection does not sufficiently take effect under moderate conditions, thus possibly impairing the performance of subsequent PCR, etc. Meanwhile, when amidites for nucleic acid synthesis (A amidite, G amidite and C amidite) used consist entirely of the amidites for nucleic acid synthesis of the present invention, protective groups in all the amidites for nucleic acid synthesis are removed similarly to one another under moderate conditions, which is advantageous in that subsequent PCR, etc. can be efficiently conducted.

In the nucleic acid synthesizing method, the amidite for nucleic acid synthesis undergoes a condensation reaction, and then a protective group in the amidite for nucleic acid synthesis is removed. Conditions that the deprotection is under are not limited to particular conditions, and suitable conditions can be selected according to the purpose, but it is desirable that the protective group be removed under such moderate conditions as described above; for example, it is desirable that the protective group be removed by a bulky base in an aprotic solvent. The aprotic solvent and the bulky base are similar to those described above. Also, the concentration and the time required for the deprotection are similar to those described above.

Since the nucleic acid synthesizing method uses the amidite for nucleic acid synthesis of the present invention, it is possible to remove a protective group in the amidite for nucleic acid synthesis under such moderate conditions as described above. Accordingly, it is possible to swiftly synthesize functional artificial nucleic acids such as primers and probes, for example using a conventional automatic nucleic acid synthesizer, and also to easily introduce unstable molecules such as fluorescent labels when the primers and probes are synthesized.

It should be noted that nucleic acids obtained by the nucleic acid synthesizing method can be suitably applied to a variety of uses without any limitation in particular; for example, the nucleic acids can be suitably used as functional nucleic acids such as PCR primers, sequencing primers, hybridization probes, antisense DNAs and siRNAs.

EXAMPLES

The following explains Examples of the present invention; however, it should be noted that the present invention is not confined to these Examples in any way.

Example 1

Synthesis of Amidite for Nucleic Acid Synthesis

The amidites for nucleic acid synthesis IIIa, IIIg and IIIc of the present invention were synthesized in the following manner. Note that the amidites for nucleic acid synthesis IIIa, IIIg and IIIc are amidites for nucleic acid synthesis corresponding to the ones represented by Structural Formulae (1), (2) and (3) above, respectively.

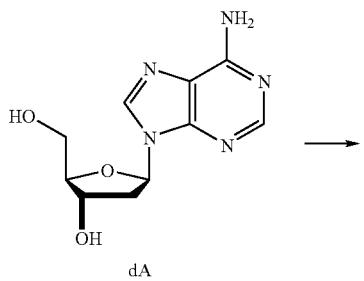

-continued
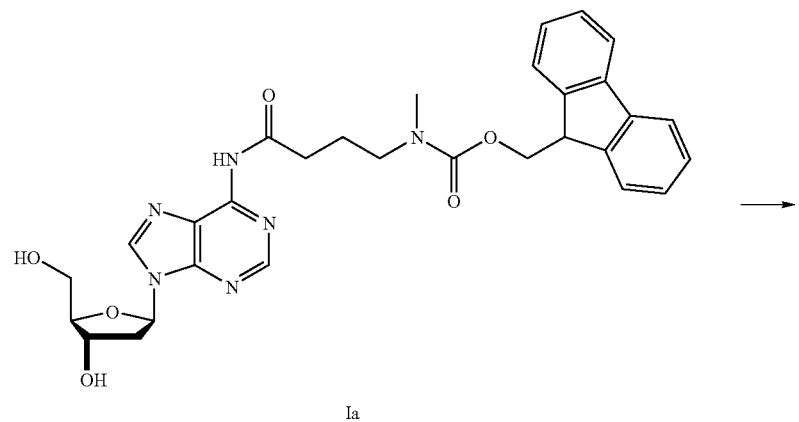
Ia
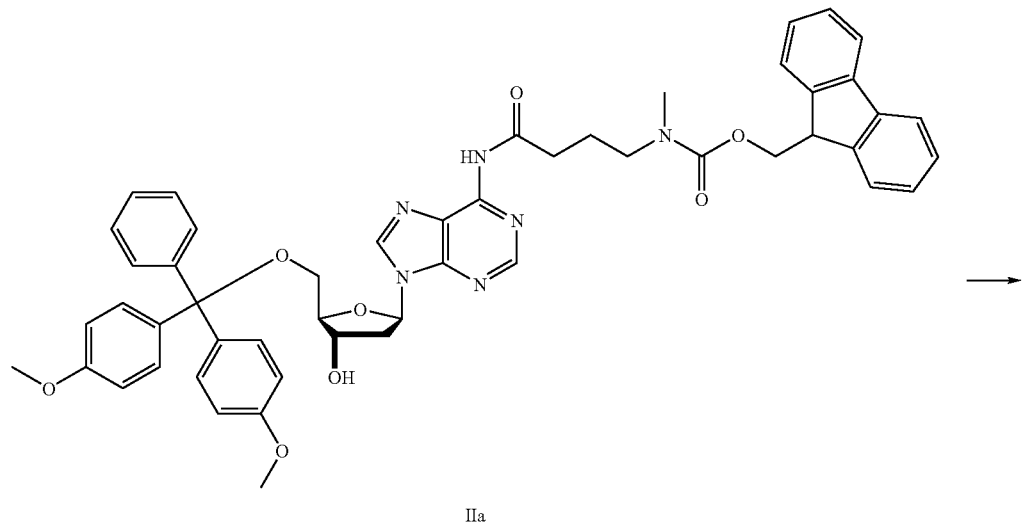
IIa
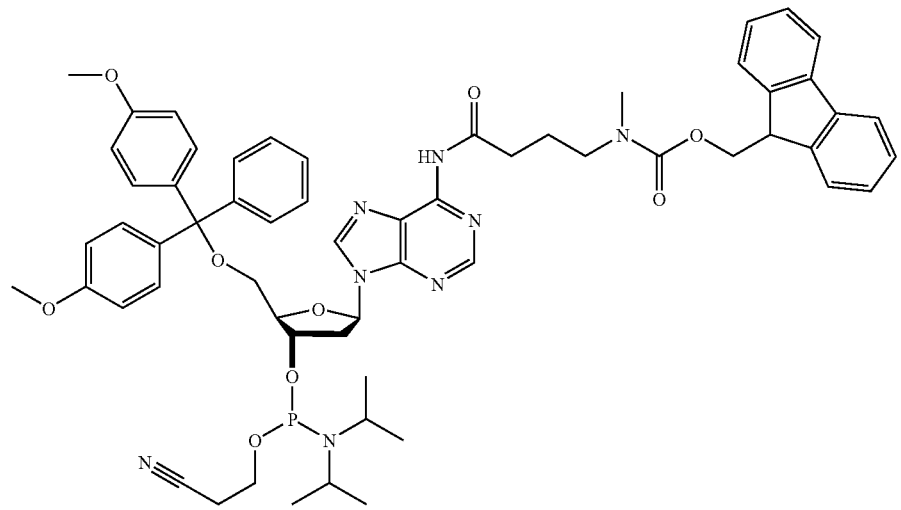
IIIa

-continued
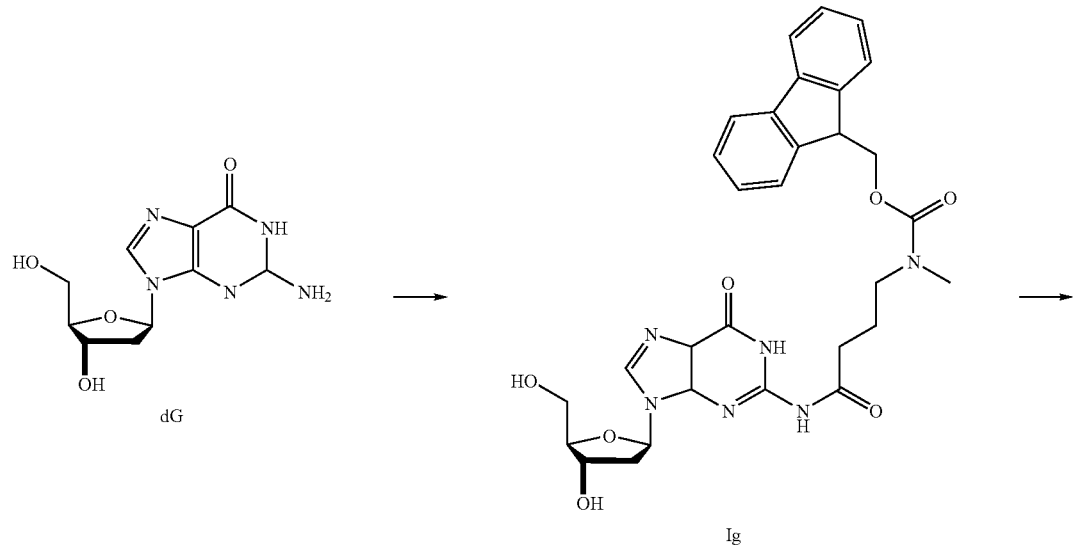
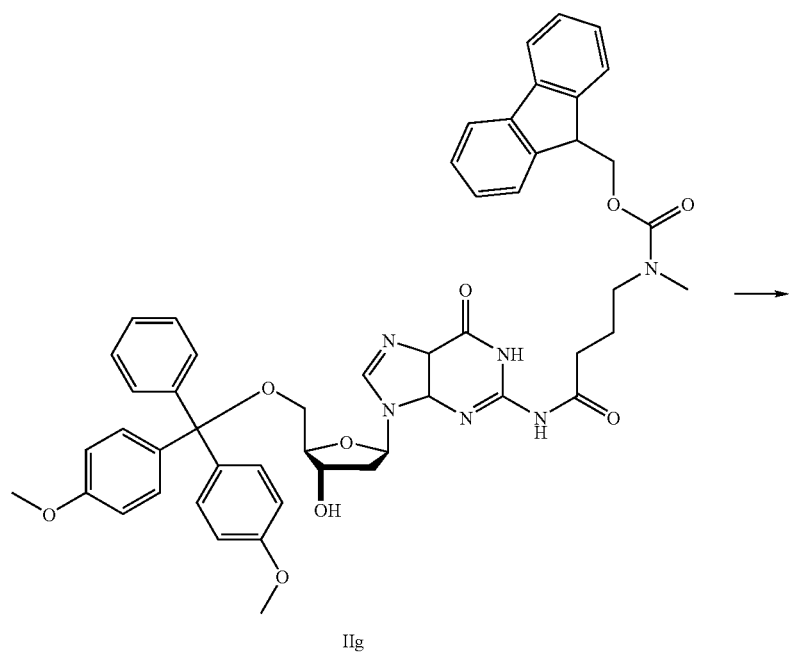

-continued
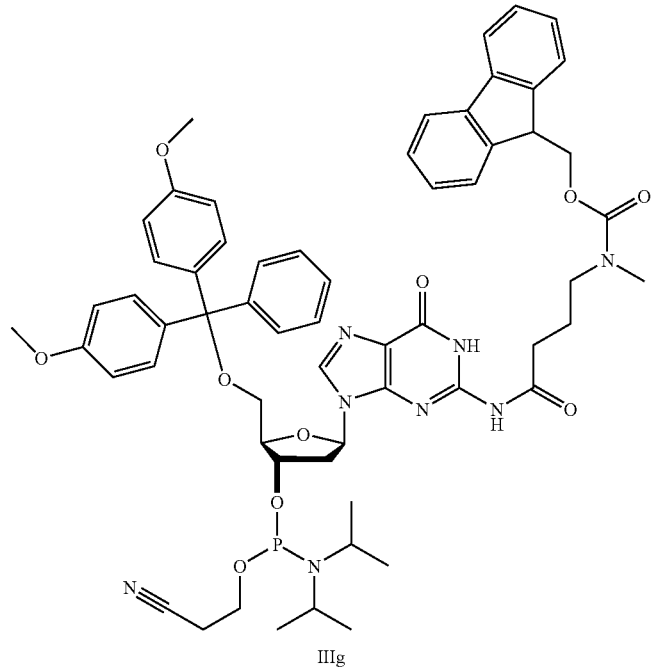
IIIg
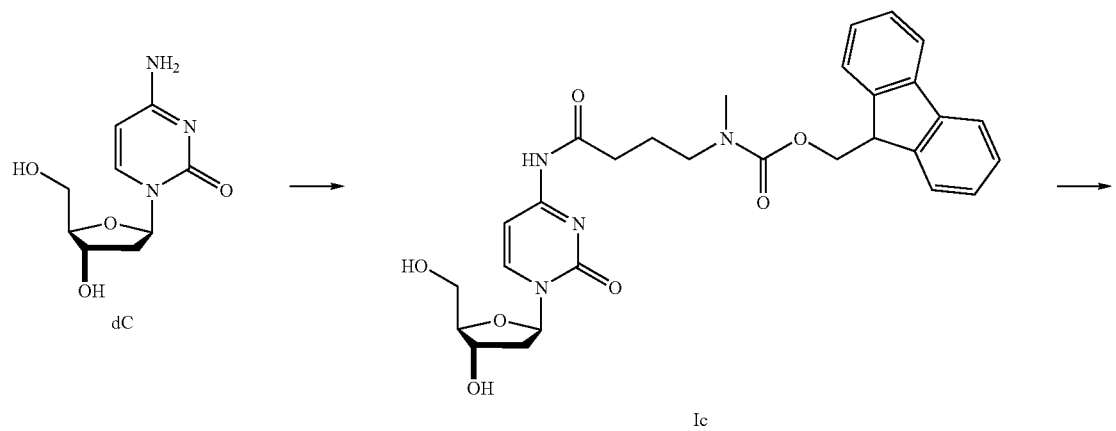
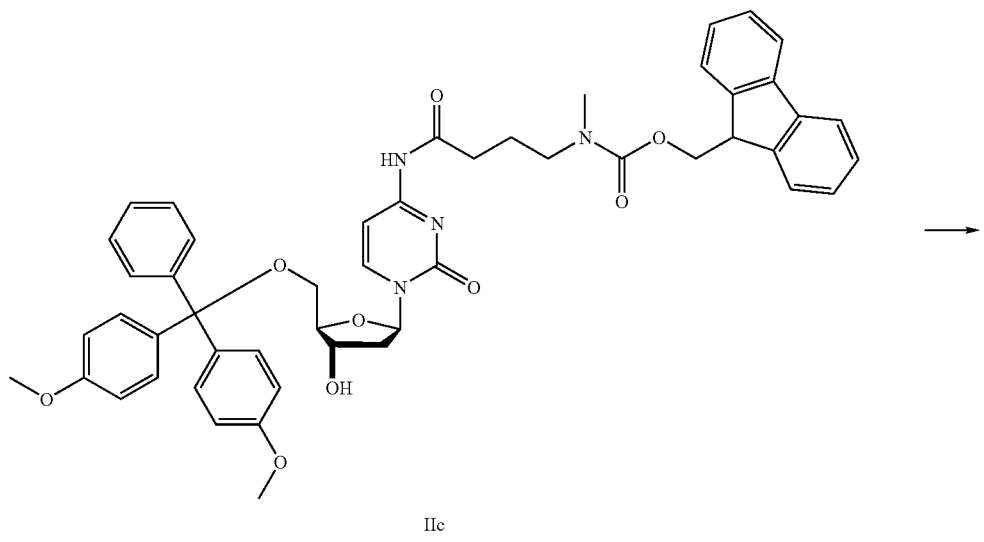

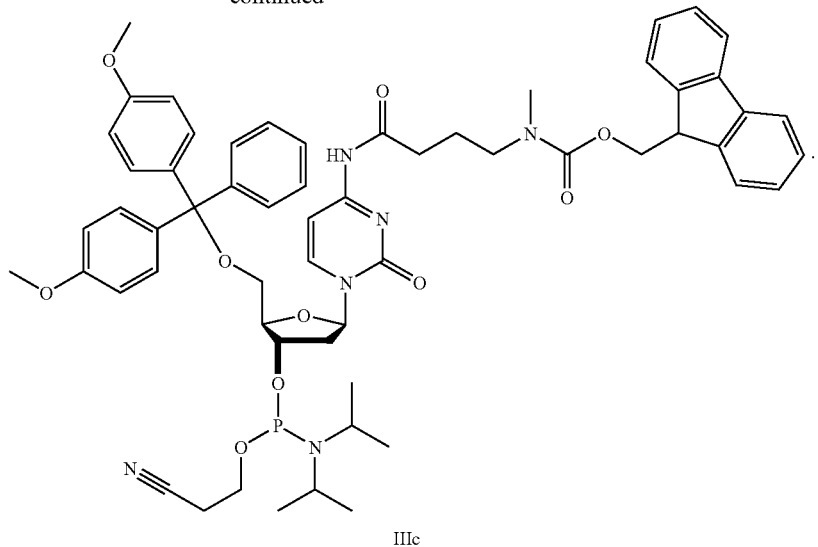

IIIc

<Synthesis of Ia, Ig and Ic>

7.68 g (50 mmol) of N-methylamino butyric acid hydrochloride was dissolved in 50 mL of water, 4.20 g (50 mmol) of NaHCO$_3$ was added, and all of these were agitated for 10 min. This solution was agitated for two days at room temperature, with 13.49 g (40 mmol) of 9-fluorenylmethyl succinimidyl carbonate, 100 mL of acetonitrile and 0.14 g (0.4 mmol) of tetrabutylammonium hydrogen sulfide added. After being concentrated under reduced pressure, the solution was diluted with methylene chloride and washed with water. After being concentrated under reduced pressure and subjected twice to azeotropy with dehydrated acetonitrile, the methylene chloride solution was subjected to azeotropy with dehydrated methylene chloride. A residue was dissolved in 200 mL of dehydrated methylene chloride, 4.13 g (20 mmol) of N,N'-dicyclohexylcarbodiimide was added at 0° C., and all of these were agitated for 2 hr at room temperature. After unnecessary materials were filtered out, this solution was concentrated under reduced pressure, and a residue A was obtained.

A deoxynucleoside (dA, dG or dC, 20 mmol) was suspended in dehydrated pyridine, and these were concentrated under reduced pressure three times. A residue was suspended in 100 mL of dehydrated pyridine, 8.45 mL (66 mmol) of trimethylchlorosilane was added at 0° C., all of these were agitated for 1 hr at room temperature and then cooled to 0° C. again, and this solution was introduced into the residue A. A reaction mixture was agitated for 2 hr at room temperature. With 20 mL of water added under ice-cold conditions, the reaction mixture was then agitated overnight at room temperature. This solution was diluted with methylene chloride and washed with water. The methylene chloride solution was concentrated under reduced pressure, and a residue was purified by medium-pressure chromatography (dichloromethane-ethanol 19:1 → 4:1) to yield desired products: 6.91 g (60%) of Ia, 9.43 g (80%) of Ig and 8.80 g (80%) of Ic.

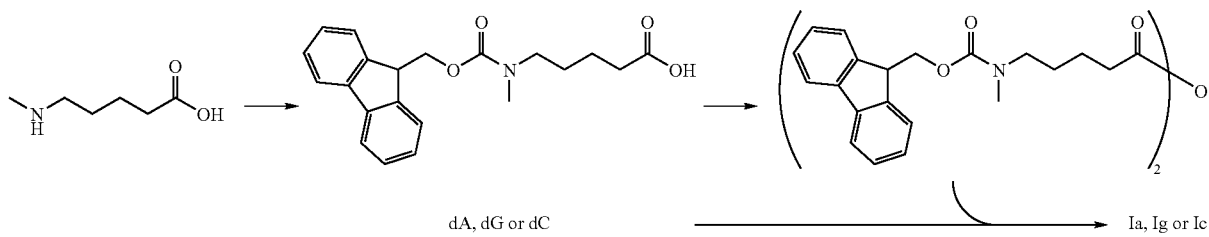

<Synthesis of IIa, IIg and IIc>

10 mmol of Ia, Ig or Ic was dissolved in dehydrated pyridine and concentrated under reduced pressure three times. A residue was dissolved in 50 mL of dehydrated pyridine, 3.36 g (10.5 mmol) of 4,4'-dimethoxytrityl chloride was added under ice-cold conditions, then all of these were agitated for 4 hr at room temperature. Subsequently, 10 mL of methanol was added, and the solution was agitated for 30 min. The solution was concentrated under reduced pressure, diluted with methylene chloride and washed with water. The methylene chloride solution was concentrated under reduced pressure, and a residue was purified by medium-pressure chromatography (dichloromethane-ethanol 98:2 → 9:1) to yield desired products: 7.92 g (91%) of IIa, 8.35 g (94%) of IIg and 7.64 g (90%) of IIc.

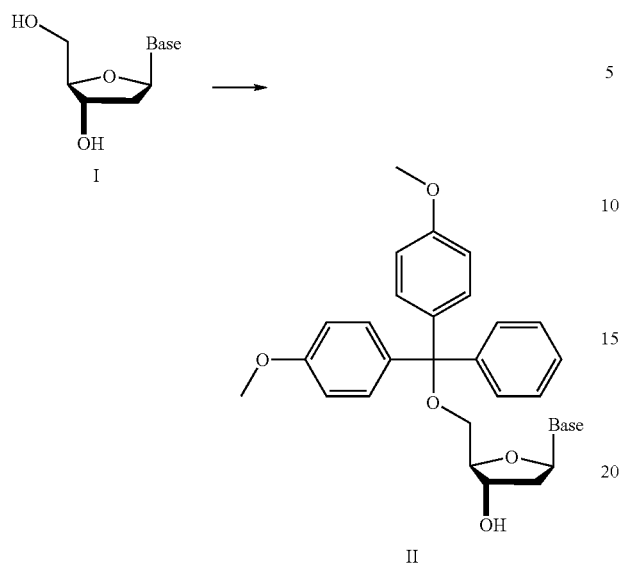

I

II

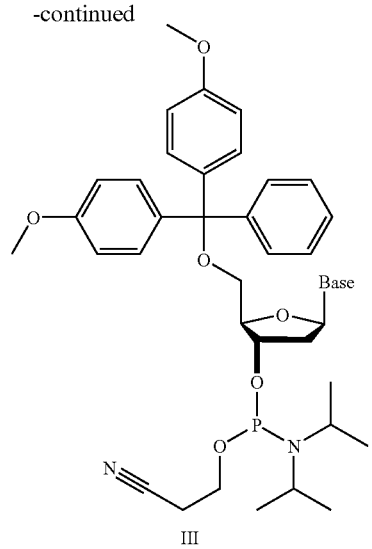

-continued

III

<Synthesis of IIIa, IIIg and IIIc>

5 mmol of IIa, IIg or IIc was dissolved in a mixed solution of dehydrated acetonitrile and dehydrated dichloromethane and concentrated under reduced pressure three times. A residue was dissolved in 20 mL of dehydrated dichloromethane, 30.5 mg (0.25 mmol) of dimethylaminopyridine and 1.05 mL (6.0 mmol) of diisopropylethylamine were added under ice-cold conditions, then 5 mL of methylene chloride solution containing 1.23 mL (5.5 mmol) of 2-cyanoethyldiisopropyl-chlorophosphoramidite was added dropwise over 15 min. The mixed solution was agitated for 2 hr at 0° C. (for IIa and IIc) or at room temperature (for IIg). Subsequently, the mixed solution was agitated for 30 min with 5 ml of methanol added. The solution was concentrated under reduced pressure, diluted with ethyl acetate and washed with water. The ethyl acetate solution was concentrated under reduced pressure, a residue was dissolved in 25 mL of ethyl acetate, and the ethyl acetate containing the residue was added dropwise to 500 mL of hexane over 15 min at −30° C. Undissolved materials were filtered out and washed with cooled hexane, and a solvent was removed under pressure from the filter cake to yield desired products: 5.22 g (97%) of IIIa, 5.22 g (96%) of IIIg and 4.70 g (94%) of IIIc.

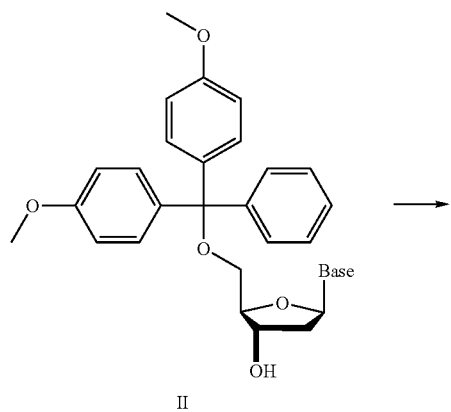

II

<Structural Confirmation of Compounds>

The structures of the compounds Ia, Ig, Ic to IIIa, IIIg, IIIc were confirmed in the following manner. The results are shown in FIGS. 1 to 12.

[$^1$H-NMR]

Approximately 10 mg of each sample was dissolved in a deuterated solvent, and a $^1$H-NMR spectrum was measured. An internal standard was based on a solvent peak.

[$^{31}$P-NMR]

PPh$_3$ was used as an external standard, and a $^{31}$P-NMR spectrum was measured with −6.2 ppm being a reference value. The measurement was carried out by BCM.

Example 2

Confirmation of Deprotection in DNA Synthesis 1

The fact that protective groups in the amidites for nucleic acid synthesis synthesized in Example 1 above can be removed under moderate conditions was confirmed in the following manner. As shown in Conditions 1 to 4 below, 5'-dGpApCpTp C3 SS CPG was synthesized using the amidites without conducting a capping operation, and the protective groups in the amidites were removed.

Additionally, dT amidite, benzoyl-protected dA amidite, benzoyl-protected dC amidite, isobutyryl-protected dG amidite, 3'-thiol-modifier C3 S-S CPG, phenoxyacetyl-protected dA amidite, acetyl-protected dC amidite and 4-isopropyl-phenoxyacetyl protected dG amidite used here in Example 2 were purchased from Glen Research Corp. Tris (2-carboxyethyl)phosphine hydrochloride (TCEP) was purchased from Sigma-Aldrich Co. A DNA synthesizer H8-F by GeneWorld Limited was used for DNA synthesis, without altering a synthesis program attached.

—Condition 1 (Contrast Area)—

5'-dGpApCpTp C3 SS CPG was synthesized using dT amidite, benzoyl-protected dA amidite, benzoyl-protected dC amidite and isobutyryl-protected dG amidite. This CPG was collected to a screw-capped tube, and heated for 8 hr at 55° C. with 28% of ammonia water added, then the solvent was distilled off under reduced pressure, and a residue was undisturbedly placed for 30 min at room temperature with 500 μl of 0.1M TCEP-tris pH=7.0 added. A portion of this solution was analyzed by HPLC. (Analysis Condition: column 5C18 column A solvent: 100 mM ammonium formate, B solvent: acetonitrile B 5%→35% (20 min) linear gradient)

Figure 13:
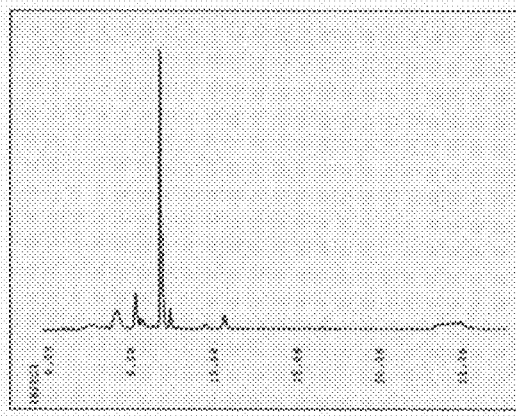
FIG. 13 shows HPLC analyses of DNA compounds under conditions 1 to 4 in Example 2.
Figure 13:
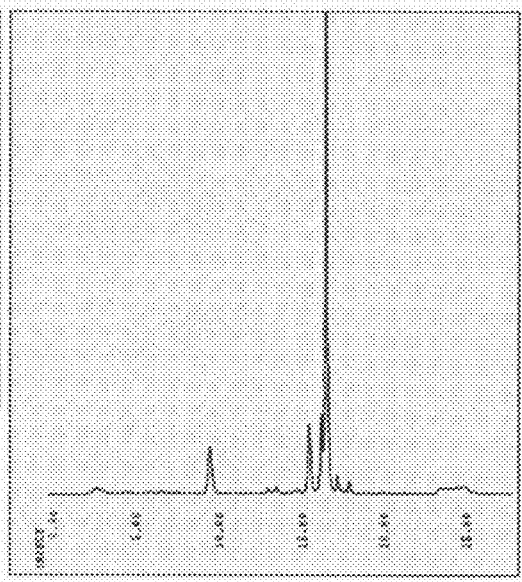
Figure 13:
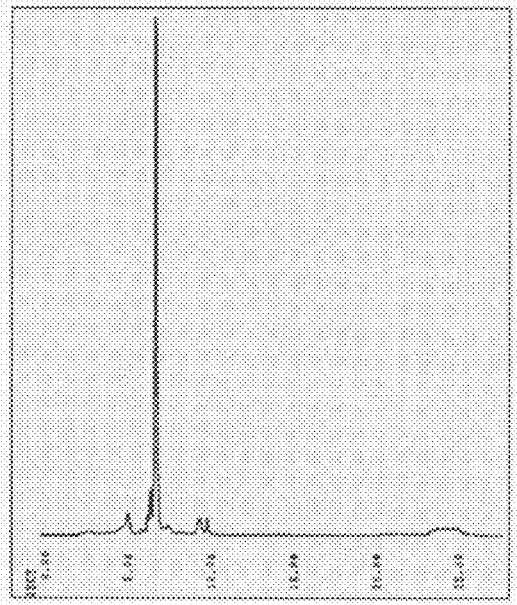
Figure 13:
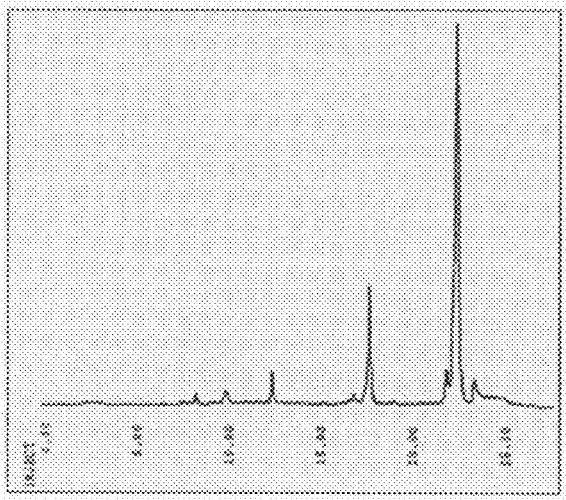
Figure 14:
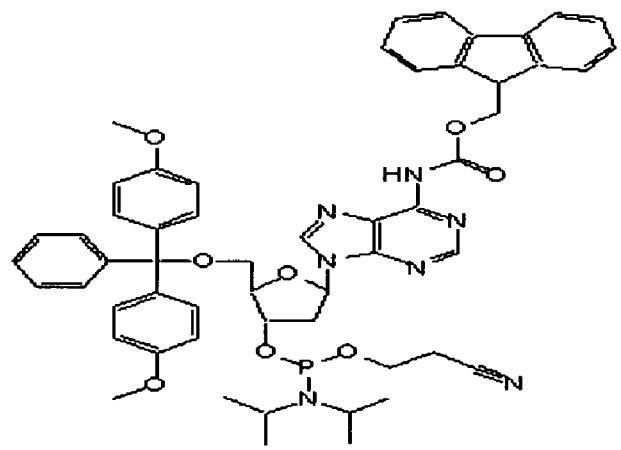
FIG. 14 shows conventional amidites for nucleic acid synthesis (Structural Formulae (4) to (6)).
Figure 14:
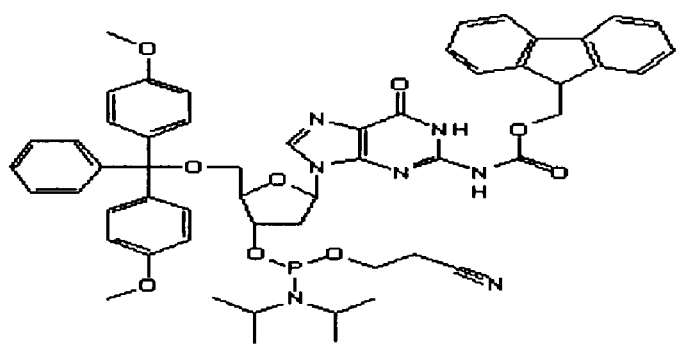
Figure 14:
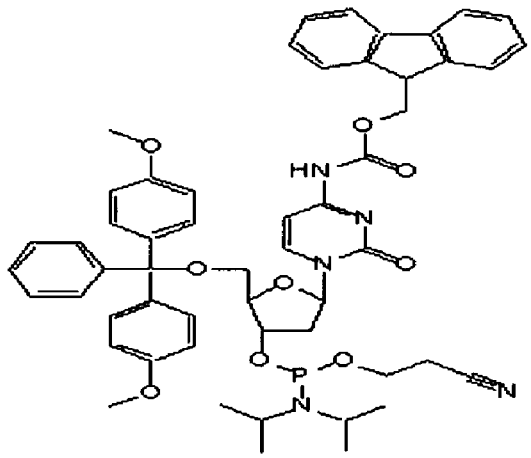
Figure 15:
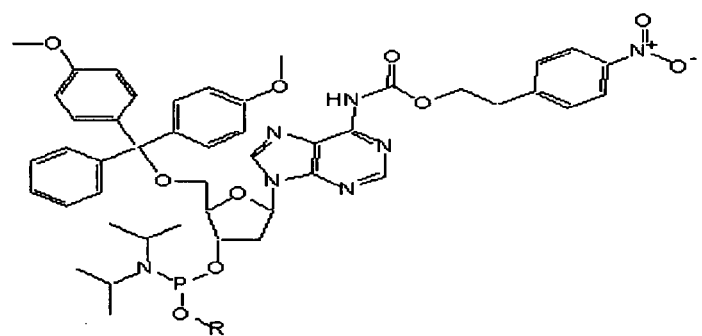
FIG. 15 shows conventional amidites for nucleic acid synthesis (Structural Formulae (7) to (9)).
Figure 15:
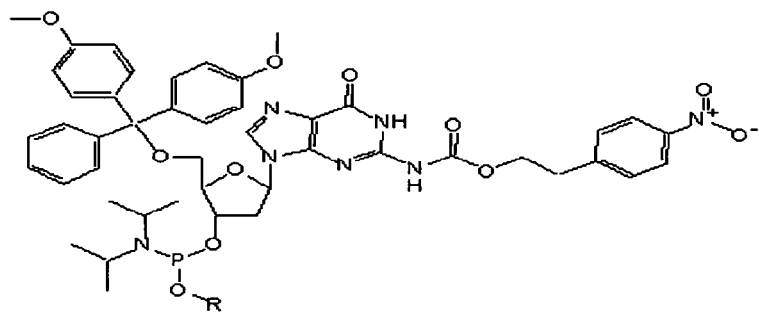
Figure 15:
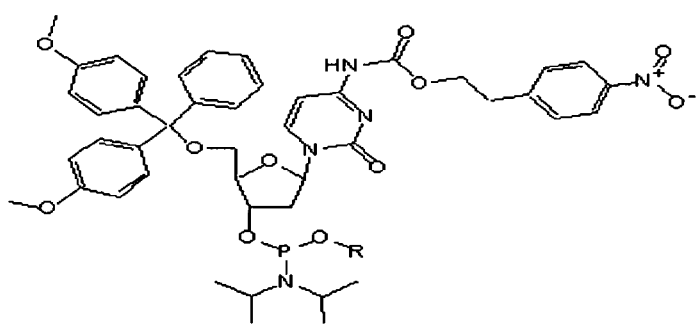
Figure 15:
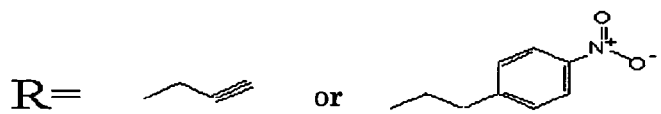
Figure 16:
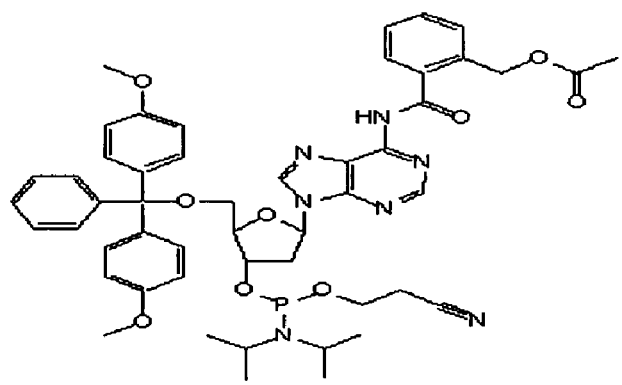
FIG. 16 shows conventional amidites for nucleic acid synthesis (Structural Formulae (10) to (12)).
Figure 16:
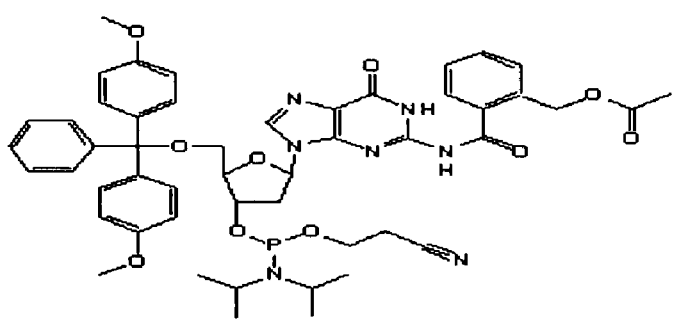
Figure 16:
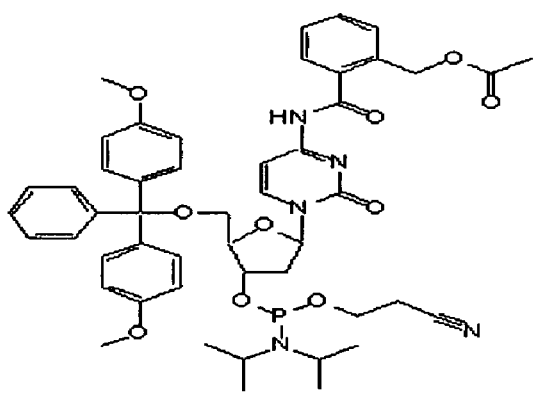

The analyses are shown in FIG. 13.

—Condition 2 (Experimental Area)—

5'-dGpApCpTp C3 SS CPG was synthesized using dT amidite and IIIa, IIIg, IIIc (amidites for nucleic acid synthesis of the present invention synthesized in Example 1). 5 mL of 0.01M DBU acetonitrile solution was applied to this DNA synthesis column for 1 hr, then it was washed with acetonitrile and water, 250 μl of 0.1M TCEP-tris (pH=7.0) was subsequently applied for 2 hr, and the solution was collected. A portion of this solution was analyzed by HPLC. (Analysis Condition: column 5C18 column A solvent: 100 mM ammonium formate B solvent: acetonitrile B 5%→35% (20 min) linear gradient)

The analyses are shown in FIG. 13.

—Condition 3 (Comparative Contrast Area)—

5'-dGpApCpTp C3 SS CPG was synthesized using dT amidite, benzoyl-protected dA amidite, benzoyl-protected dC amidite and isobutyryl-protected dG amidite. 5 mL of 0.01M DBU acetonitrile solution was applied to this DNA synthesis column for 1 hr, then it was washed with acetonitrile and water, 250 μl of 0.1M TCEP-tris pH=7.0 was subsequently applied for 2 hr, and the solution was collected. A portion of this solution was analyzed by HPLC. (Analysis Condition: column 5C18 column A solvent: 100 mM ammonium formate B solvent: acetonitrile B 5%→35% (20 min) linear gradient)

The analyses are shown in FIG. 13.

—Condition 4 (Comparative Contrast Area)—

5'-dGpApCpTp C3 SS CPG was synthesized using dT amidite, phenoxyacetyl-protected dA amidite, acetyl-protected dC amidite and 4-isopropyl-phenoxyacetyl protected dG amidite. 5 mL of 0.01M DBU acetonitrile solution was applied to this DNA synthesis column for 1 hr, then it was washed with acetonitrile and water, 250 μl of 0.1M TCEP-tris pH=7.0 was subsequently applied for 2 hr, and the solution was collected. A portion of this solution was analyzed by HPLC. (Analysis Condition: column 5C18 column A solvent 100 mM ammonium formate B solvent acetonitrile B 5%→35% (20 min) linear gradient)

The analysis result is shown in FIG. 13.

Consequently, since the retention times of main products are equal only in Conditions 1 and 2 (FIG. 13), it became clear that only in DNA synthesis using the IIIa, IIIg and IIIc (amidites for nucleic acid synthesis of the present invention synthesized in Example 1), deprotection was possible in 1 hr in 0.01M DBU acetonitrile solution. Also, in Condition 2, it was found that the product amount was small except at a main peak as in Condition 1, and that alkylation of a base could be ignored in the present condition.

Example 3

Confirmation of Deprotection in DNA Synthesis 2

The fact that protective groups in the amidites for nucleic acid synthesis synthesized in Example 1 above can be removed under moderate conditions was further confirmed in the following manner.

ABI381A manufactured by Applied Biosystems was used as an automatic DNA synthesizer, and IIIa, the IIIc, the IIIg and T amidite were synthesized in this order to 3'-thiol-modifier C3 S-S CPG purchased from Glen Research Corp. As a synthesis cycle was used as it was without modification, synthesis was made possible with a yield of 98% or more at each stage. "DNA solution A" was obtained by applying 200 μl of 0.01M DBU to this resin for 15 min and then applying 400 μl of 0.1M DTT solution for 4 hr.

Meanwhile, as a control, A amidite, C amidite, G amidite and T amidite were synthesized in this order with respect to similar 3'-thiol-modifier C3 S-S CPG, deprotection and excision were conducted by means of ammonia water in the presence of DTT in accordance with a prescribed rule to yield "DNA solution B".

As a result of comparing the solutions A and B by HPLC, it was found that main products were identical. Also, it was confirmed that a protective group was stable in a mixed solution of DTT water and pyridine as the compounds Ia and Ig were used. Consequently, it became clear that protective groups in the IIIa, IIIc and IIIg (amidites for nucleic acid synthesis represented by Structural Formulae (1), (2) and (3) above) could be removed in 15 min in 200 μl of 0.01M DBU.

Since the amidite for nucleic acid synthesis of the present invention enables a protective group therein to be removed under moderate conditions, the amidite for nucleic acid synthesis can be suitably used in a nucleic acid synthesizing method of the present invention, for example.

Also, since the nucleic acid synthesizing method of the present invention makes it possible to remove a protective group in the amidite for nucleic acid synthesis under moderate conditions, the nucleic acid synthesizing method can be suitably used in synthesizing functional nucleic acids such as PCR primers, sequencing primers, hybridization probes, antisense DNAs and siRNAs, for example.

What is claimed is:

1. An amidite for nucleic acid synthesis, represented by General Formula (I) below:

General Formula (I)

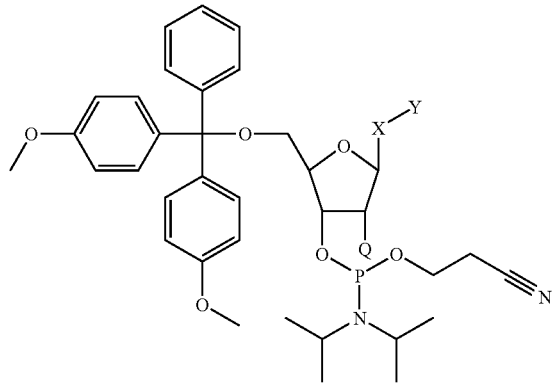

where X denotes a base; Y denotes a protective group represented by General Formula (II) below;

General Formula (II)

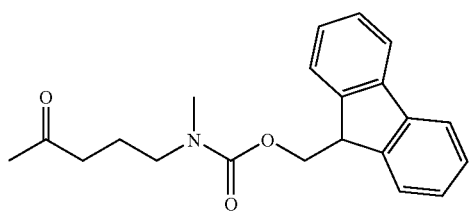

and Q denotes one of a hydrogen atom and a hydroxyl group.

2. The amidite for nucleic acid synthesis according to claim 1, wherein the base denoted by X in General Formula (I) is any one of adenine, guanine and cytosine.

3. The amidite for nucleic acid synthesis according to claim 1, wherein the protective group denoted by Y in General Formula (I) is bonded to an exocyclic amino group in the base denoted by X.

4. The amidite for nucleic acid synthesis according to claim 1, represented by any one of Structural Formulae (1) to (3) below.

Structural Formula (1)

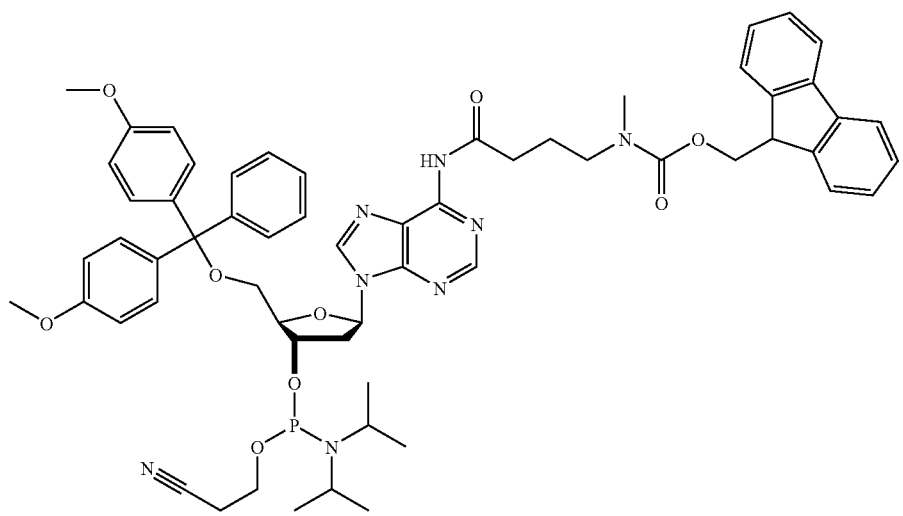

Structural Formula (2)

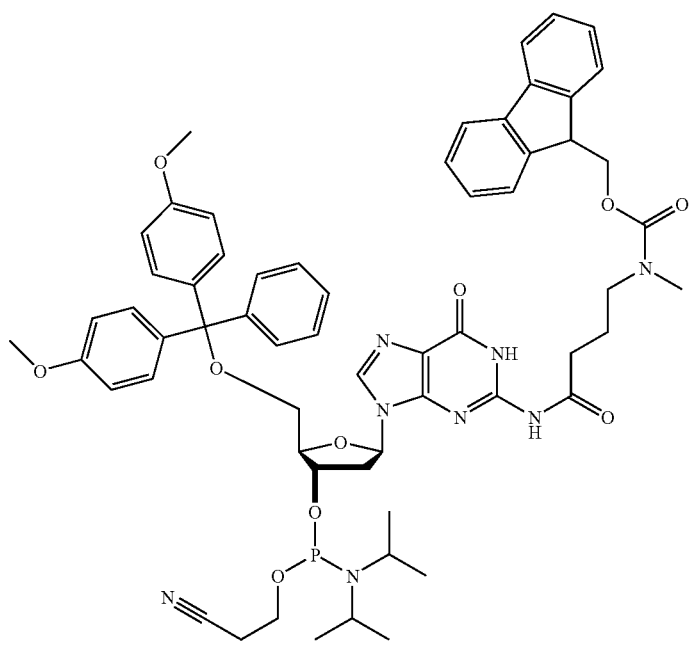

-continued

Structural Formula (3)

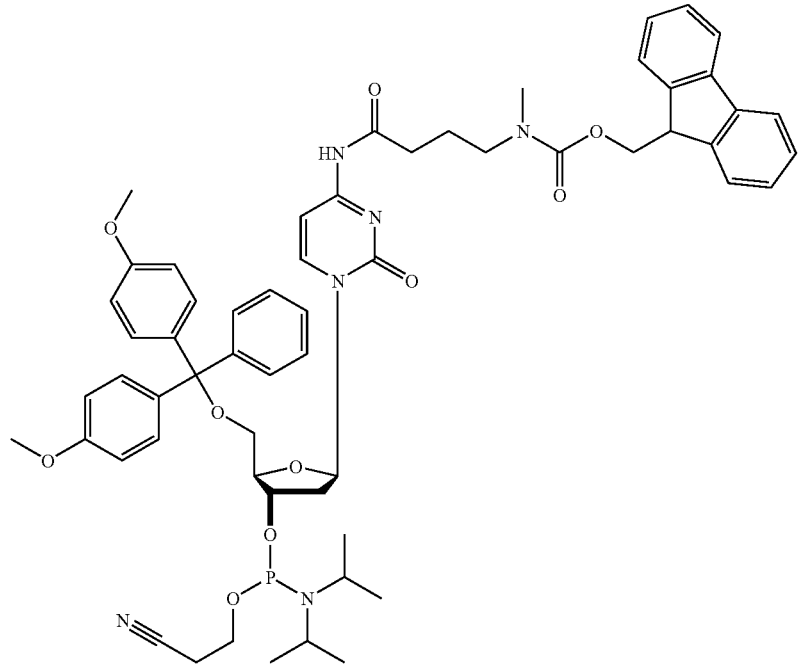

5. The amidite for nucleic acid synthesis according to claim 1, wherein the protective group can be removed in an aprotic solvent.

6. The amidite for nucleic acid synthesis according to claim 5, wherein the aprotic solvent is at least one selected from the group consisting of acetonitrile, dichloromethane, DMF and N-methylpyrrolidone.

7. The amidite for nucleic acid synthesis according to claim 1, wherein the protective group can be removed by a bulky base.

8. The amidite for nucleic acid synthesis according to claim 7, wherein the bulky base is at least one selected from the group consisting of DBU, DBN and tetramethylguanidine.

9. The amidite for nucleic acid synthesis according to claim 1, wherein the protective group can be removed at a DBU concentration of 0.01M or less.

10. The amidite for nucleic acid synthesis according to claim 1, wherein the protective group can be removed within 15 mm.

11. A nucleic acid synthesizing method comprising:
using an amidite for nucleic acid synthesis represented by General Formula (I) below, General Formula (I)

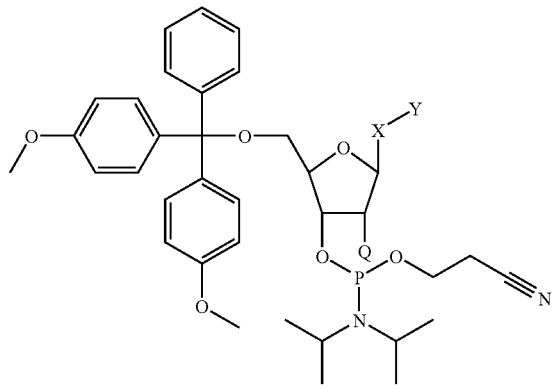

where X denotes a base; Y denotes a protective group represented by General Formula (II) below;

General Formula (II)

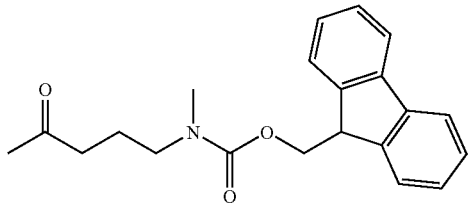

and Q denotes one of a hydrogen atom and a hydroxyl group.

12. The nucleic acid synthesizing method according to claim 11, wherein the amidite for nucleic acid synthesis undergoes a condensation reaction, and then the protective group in the amidite for nucleic acid synthesis is removed.

13. The nucleic acid synthesizing method according to claim 11, wherein the protective group is removed in an aprotic solvent.

14. The nucleic acid synthesizing method according to claim 13, wherein the aprotic solvent is at least one selected from the group consisting of acetonitrile, dichloromethane, DMF and N-methylpyrrolidone.

15. The nucleic acid synthesizing method according to claim 11, wherein the protective group is removed by a bulky base.

16. The nucleic acid synthesizing method according to claim 15, wherein the bulky base is at least one selected from the group consisting of DBU, DBN and tetramethylguanidine.

17. The nucleic acid synthesizing method according to claim 11, wherein the protective group is removed at a DBU concentration of 0.01M or less.

18. The nucleic acid synthesizing method according to claim 11, wherein the protective group can be removed within 15 min.

19. The nucleic acid synthesizing method according to claim 11, wherein nucleic acid synthesis is conducted using an automatic nucleic acid synthesizer.

* * * * *